US010634630B2

(12) United States Patent
Paproski

(10) Patent No.: US 10,634,630 B2
(45) Date of Patent: Apr. 28, 2020

(54) LOW-FIELD TIME-DOMAIN NMR MEASUREMENT OF OIL SANDS PROCESS STREAMS

(71) Applicant: SYNCRUDE CANADA LTD. in trust for the owners of the Syncrude Project as such owners exist now, Fort McMurray (CA)

(72) Inventor: Richard Paproski, Edmonton (CA)

(73) Assignee: SYNCRUDE CANADA LTD., Fort McMurray (CA), in trust for the owners of the Syncrude Projects as such owners exist now and in the future (*) Notice: Subject to any disclaimer, the term of this patent is extended or adjusted under 35 U.S.C. 154(b) by 609 days.

(21) Appl. No.: 15/477,961

(22) Filed: Apr. 3, 2017

(65) Prior Publication Data

US 2017/0292924 A1 Oct. 12, 2017

Related U.S. Application Data

(60) Provisional application No. 62/321,605, filed on Apr. 12, 2016.

(51) Int. Cl.
 *G01R 33/48* (2006.01)
 *G01N 24/08* (2006.01)
 (Continued)

(52) U.S. Cl.
 CPC ......... *G01N 24/082* (2013.01); *G01N 24/081* (2013.01); *G01N 33/2823* (2013.01);
 (Continued)

(58) Field of Classification Search
 CPC .... G01N 24/081; G01N 24/08; G01N 24/082; G01N 24/10; G01V 3/32; A61B 5/055;
 (Continued)

(56) References Cited

U.S. PATENT DOCUMENTS

| 5,557,200 A | 9/1996 | Coates |
| 6,646,437 B1 | 11/2003 | Chitale et al. |

(Continued)

FOREIGN PATENT DOCUMENTS

| CA | 2708557 A1 | 12/2011 |
| CA | 2912668 | 11/2014 |

OTHER PUBLICATIONS

Hum, F.M., Kantzas, A., "Clarifying the contribution of clay bound water and heavy oil to NMR spectra of unconsolidated samples" (2007) Journal of Canadian Petroleum Technology, 46 (7) 37-42.

(Continued)

*Primary Examiner* — Alesa Allgood
(74) *Attorney, Agent, or Firm* — Bennett Jones LLP

(57) ABSTRACT

A method for determining the solids content, fines content and/or particle size distribution of the solids in an oil sands process stream test sample comprising bitumen, solids and water using low-field time-domain NMR is provided which involves building a non-solids partial least squares calibration model using oil sands process streams calibration samples having a known bitumen content, solids content, water content, fines content and/or particle size distribution by subjecting the calibration samples to a first $T_1$-weighted $T_2$ measurement NMR pulse sequence that maximizes very fast relaxing signals and a second T1-weighted T2 measurement NMR pulse sequence that maximizes slow relaxing signals. The measurement of other sample properties strongly correlated with surface area, such as methylene blue index, can also be measured using a partial least squares calibration model.

22 Claims, 26 Drawing Sheets

(51) Int. Cl.
*G01R 33/44* (2006.01)
*G01N 33/28* (2006.01)
*G01R 33/50* (2006.01)

(52) U.S. Cl.
CPC ....... *G01R 33/448* (2013.01); *G01R 33/4828* (2013.01); *G01R 33/50* (2013.01)

(58) Field of Classification Search
CPC ............................ G01R 33/50; G01R 33/4828; G01R 33/5608; G01R 33/4816
See application file for complete search history.

(56) References Cited

U.S. PATENT DOCUMENTS

| | | | |
|---|---|---|---|
| 7,397,241 B2* | 7/2008 | Gauthausen | G01R 33/46 324/300 |
| 7,417,426 B2 | 8/2008 | Race et al. | |
| 8,195,399 B2* | 6/2012 | Gladkikh | G01V 3/32 324/303 |
| 8,547,096 B2 | 10/2013 | Kamar et al. | |
| 8,653,815 B2 | 2/2014 | Chapura et al. | |
| 9,671,516 B2* | 6/2017 | Venkataramanan | G01R 33/448 |
| 10,061,052 B2* | 8/2018 | Chen | G01N 24/081 |
| 2008/0221800 A1* | 9/2008 | Gladkikh | G01V 3/32 702/11 |
| 2010/0315081 A1 | 12/2010 | Chapura et al. | |
| 2013/0057277 A1 | 3/2013 | Zielinski et al. | |
| 2014/0132259 A1 | 5/2014 | Song | |
| 2016/0231451 A1* | 8/2016 | Chen | G01N 24/081 |

OTHER PUBLICATIONS

Jin, Y., Zheng, X., Chi, Y., Ni, M. "Rapid, accurate measurement of the oil and water contents of oil sludge using low-field NMR," 2013 Industrial and Engineering Chemistry Research 52 (6) pp. 2228-2233.

Motta Cabrera, S.C., Bryan, J., Kantzas, A., "Estimation of bitumen and solids content in tine tailings using low-field NMR technique" (2010) Journal of Canadian Petroleum Technology, 49 (7) 8-19.

Motta Cabrera, S.C, Bryan, J., Komishke, B., Kantzas, A., "Study of the settling characteristics of tailings using magnetic resonance technique" (2009) International Journal of Mining, Reclamation, and Environment, 23 (1) 33-50.

Thoma, Steven B.; Smith, Douglas M.; Boughton, John; Davies, Reg, "On-line surface area measurement of concentrated slurries using low field spin-lattice relaxation NMR" (1993) Particle and Particle Systems Characterization, 10 (5) 246-251.

Mashburn, K.E., Birdwell, J.E. "Updated methodology for nuclear magnetic resonance characterization of shales," 2013 Journal of Magnetic Resonance 233 pp. 17-28.

* cited by examiner

LOW-FIELD TIME-DOMAIN NMR MEASUREMENT OF OIL SANDS PROCESS STREAMS

FIELD OF THE INVENTION

The present invention relates to a method for determining the solids content, the fines content (e.g., particles having a diameter less than a given particle diameter, such as <44 micron), and/or the particle size distribution of solids/fines in an oil sand process sample. More particularly, low-field time-domain nuclear magnetic resonance (low-field TD-NMR) is used to quickly quantify the concentrations of solids and fine particles (in addition to bitumen and water), using optimized pulse sequences that utilize both the longitudinal relaxation ($T_1$) and the transverse relaxation ($T_2$) contrasts between the bitumen and water in the sample. The sample weight less the amount of non-solids as determined by a non-solids partial least squares calibration model is the basis for the % solids measurement. The strong effect that fine particles have on the relaxation rate of water and a partial least squares calibration model for fine particles are the basis for the measurement of % fine particles in the sample. The measurement of other sample properties strongly correlated with surface area, such as methylene blue index, can also be measured using a partial least squares calibration model.

BACKGROUND OF THE INVENTION

Oil sand process streams comprise bitumen (a heavy oil), water, and mineral solids of various particle sizes. As used herein, "oil sands process stream" means any stream produced during the extraction of bitumen from oil sands, including tailings streams and streams produced during the treatment of tailings prior to reclamation. The composition of such streams can have a strong impact on the recovery of bitumen during the hot water extraction process of oil sand slurry. For example, it is well known that high concentrations of fine particles can have a negative impact on the recovery of bitumen, and that the dosage of process aids, such as caustic, can be adjusted to help mitigate poor bitumen recovery if the amount of fine particles can be determined. The tailings streams from the extraction process segregate in settling basins, forming clarified process water for reuse, sand beaches, and a material high in water and fine solids content known as fluid fine tailings (FFT). When tailings materials are mixed with gypsum and sand to produce a non-segregating mixture (i.e. composite tailings) or mixed with polymer flocculants and gypsum and then centrifuged to produce a stronger cake material (i.e. centrifuged tailings), knowing the composition of the feed and product streams, including the concentration of fine particles, is important to produce materials that meet the required quality specifications and to optimize the dosage of process aids such as flocculant and gypsum.

The Dean-Stark extraction method is currently the industry reference method for determining the concentrations of bitumen, water, and/or solids of an oil sand process sample. A weighed sample is separated into bitumen, water, and solids by refluxing toluene in a Soxhlet extraction apparatus. Condensed toluene and co-distilled water are continuously separated in a trap designed to recycle the solvent through the extraction thimble, dissolving the bitumen present in the sample, while the water is retained in the trap. Full extraction of bitumen from the solids can often take hours to complete. Once the three components have been physically separated, they can be determined by various means.

Given the long analysis time of Dean-Stark extraction, faster methods are often used to monitor oil sand process streams. These fast methods typically sacrifice some accuracy and/or repeatability in order to achieve a shorter analysis time. They may rely on an extraction step, centrifugation step, filtration step, and/or drying step to separate various components prior to measurement, which adds to the total analysis time. Process conditions can quickly change within minutes, making ever shorter analysis times desirable.

Before particle size analysis of the mineral solids within oil sand process streams can be performed, the solids typically need to be cleaned and dried to remove the bitumen and water (e.g. by Dean-Stark extraction or repeated cold solvent washing and centrifugation followed by drying). The clean and dry solids then need to be disaggregated, dispersed in a suitable aqueous solution that results in a stable, fully dispersed suspension of fine particles, then measured by a suitable particle sizing analysis technique such as laser diffraction or wet sieve. Failure to remove the bitumen can lead to erroneous results, such as including the bitumen as part of the coarse solids, and can cause fouling issues with the particle sizing equipment.

These cleaning and measurement steps can take many hours or even days to perform to completion. It is therefore desirable to develop a faster method for quickly measuring the amount of bitumen, water, solids, and fine particles in oil sand process samples with relatively good accuracy (as compared to reference analysis methods), good precision, and within as short an analysis time as possible.

U.S. Pat. No. 8,547,096 discloses a method of quickly determining the composition of a sample including bitumen and water using low-field NMR. However, no information on the amount of fine particles is available. Also, calculating the solids content by subtracting the % bitumen and % water from 100% is not sufficiently accurate for some applications, for example, when measuring the % solids in centrifuge centrate samples when the % solids are routinely less than 5%.

U.S. Pat. No. 7,417,426 discloses a compact and portable NMR device for making a variety of NMR measurements on generic dispersions, with predictions of particle sizes and solid/liquid ratios in dispersions as some of the potential measurements that could be made. Their described methods of using a pure liquid and known samples to measure relaxation rate information to predict solid/liquid ratios, surface area, and particle size can be expected to work for simple dispersions of a single type of particle in a pure liquid. In this case, no information is provided on how to resolve the problem of overlapping signals from multiple fluids (e.g. bitumen and water). Specifically, no information is provided on how to deal with the issue of measuring overlapping signals of water-associated with fine particles and bitumen, both of which can have relaxation times on the order of milliseconds. Also, U.S. Pat. No. 7,417,426 demonstrates how the type of particle in the dispersion can have a strong impact on the measured relaxation rate for a given surface area. This complicates the prediction of particle size if there are multiple types of mineral particles (e.g. quartz, various clays, and other minerals), especially when one cannot assume that the mineral composition is consistent between different unknown samples.

U.S. Pat. No. 8,653,815 discloses a method for determining the particle size distribution of a subsurface rock formation using the relaxation data collected by a downhole NMR logging tool. This method is specific to downhole rock formations and also requires an elaborate correction procedure and potentially additional acoustic compressive strength measurements to be performed in order to achieve a certain level of agreement with reference particle sizing methods. No information is provided on how to deal with the issue of measuring overlapping signals of water-associated with fine particles and a heavy oil such as bitumen.

U.S. Patent Application No. 2014/0132259 discloses a method for determining particle size distribution of a subsurface rock formation using the relaxation data collected by a downhole NMR logging tool when there are at least two fluids present. In this case, other measurements such as electrical resistivity are needed to help determine fractional fluid volumes. Also, samples of each fluid must be collected to measure their proprieties individually at the temperature and pressure of the downhole conditions. Further, assumptions must be made as to which fluid is present in pores below a cutoff size as part of the analysis. These subsurface rock formation measurement tools are not applicable to oil sand process streams where the compositions of the samples can vary significantly from very fluid (e.g. <5% solids) to very dense (e.g. 50-80% solids).

Thus, there is a need in the industry to be able to quickly measure the composition of various oil sand process streams, in particular, the solids content and particle size of the solids to help ensure reliable operations.

SUMMARY OF THE INVENTION

The present application uses low-field time-domain nuclear magnetic resonance (low-field TD-NMR) instruments to analyze oil sand process stream samples to provide an accurate measurement of the bitumen, water, solids, and fine particles content in the process stream. In one embodiment, the present application uses TD-NMR to measure the fine particle content smaller than a given diameter (e.g. % <44 micron, % <5.5 micron, % <1.9 micron), as a percentage of the whole sample, as well as the % solids, % bitumen, and % water content of the particular process stream sample. The measurement of fine particles smaller than sizes not specifically listed herein is also possible.

As used herein, "solids content" means the concentration of solid particles having any diameter and includes both coarse and fine particles. As used herein, "fines content" means the concentration of solid particles having a diameter less than a given diameter. For example, in the oil sands industry, fine particles present in oil sands process streams are generally referred to as particles having a diameter less than about 44 μm and include clays, silt and the like. It is understood, however, that the present invention can be modified to measure fine particles having a diameter less than various individual diameters, e.g., <44 μm, <5 μm, <1 μm, etc. As used herein, "particle size distribution" means the concentration of particles having a diameter less than a number of given diameters, e.g., particles <44 μm, <5 μm, <1 μm reported either as a percentage of the whole sample or as a percentage of the solids.

The TD-NMR $T_1$-weighted $T_2$ measurement approach used here involves first aligning the nuclear spin of hydrogen atoms in a sample according to an externally applied magnetic field. A series of 90° radio-frequency pulses are initially applied to the sample to saturate the magnetization in the +Z axis. Transverse relaxation ($T_2$) echo trains are recorded after incremental longitudinal relaxation to produce a raw TD-NMR data set for the sample. Both the longitudinal ($T_1$) and transverse ($T_2$) relaxation behavior can be observed simultaneously using a carefully designed sequence of radio-frequency pulses that emphasizes the contrast between components in the sample that are to be measured. The rate of relaxation is dependent on several factors, including the mobility of the hydrogen nuclei in the sample as is known in the art.

Hydrogen nuclei in bitumen have relatively low mobility due to bitumen's high viscosity and can relax relatively quickly (e.g. milliseconds). Hydrogen nuclei in pure water have relatively high mobility due to water's low viscosity and can relax relatively slowly (e.g. up to seconds). When water is associated with fine clay solids, the water molecules can undergo surface relaxation effects that produce relaxation rates on the order of milliseconds. Surface relaxation rates tend to scale with the ratio of the surface area of the solids to the water volume, although U.S. Pat. No. 7,417,426 highlights how different types of solids can produce very different water relaxation rates for a given surface area. The combined $T_1$ and $T_2$ contrast of the raw TD-NMR data set can be used to determine the amount bitumen and water in a sample as shown in U.S. Pat. No. 8,547,096. It was surprisingly discovered that the concentration of fine particles in a test sample can be directly predicted using partial least squares models of raw TD-NMR data sets carefully optimized for fast relaxing components within the sample without the need for other time-consuming measurements or elaborate corrections. It was also discovered that highly accurate measurements of the weight % solids in the sample could be accomplished by building a single partial least squares model of the non-solids content using raw TD-NMR data sets carefully optimized for slower relaxing components within the sample, and then using the sample weight to determine the solids content by difference.

Thus, in one aspect, a method is provided for determining solids content, fines content and/or particle size distribution in an oil sands process stream test sample comprising bitumen, solids and water using low-field time-domain NMR, comprising:

building partial least squares calibration models for non-solids content and fine particles content(s) less than a given, or multiple, particle size(s) using oil sands process streams calibration samples having a known bitumen, water, and solids contents, and a known particle size distribution of the solids, by subjecting the calibration samples to a first $T_1$-weighted $T_2$ NMR pulse sequence that measures fast relaxing signals and a second $T_1$-weighted $T_2$ NMR pulse sequence that measures slow relaxing signals, based on the shift to faster water signal relaxation times as the ratio of fine particles to water in the sample is increased;

subjecting the test sample to either the first fast relaxing $T_1$-weighted $T_2$ NMR pulse sequence, the second slow relaxing $T_1$-weighted $T_2$ NMR pulse sequence, or both, and measuring the produced signal amplitudes;

determining the fine particles content and/or particle size distribution in the test sample by applying the calibration loading(s) for fine particles less than a given, or multiple, particle size(s) to the fast relaxing pulse sequence raw NMR data; and/or determining the solids content by applying the non-solids loading to the slow relaxing pulse sequence raw NMR data and calculating the solids content by difference from the sample weight.

In another aspect, a method is provided for determining the solids content, the fines content, and/or particle size distribution in an oil sands process stream test sample comprising bitumen, water, and solids using low-field TD-NMR, comprising:

(a) initially saturating the magnetization of the sample so that essentially no magnetization remains in the +Z axis by applying 10 rapid 90° radio-frequency (RF) pulses to the sample prior to each $T_1$-weighted $T_2$ measurement;
(b) subjecting the sample to either a first combined recovery and transverse relaxation sequence of NMR radio-frequency pulses comprising a $T_1$-weighted $T_2$ measurement with an emphasis on measuring faster relaxing components within the sample, a second combined recovery and transverse relaxation sequence of NMR radio-frequency pulses comprising a $T_1$-weighted $T_2$ measurement with an emphasis on measuring slower relaxing components within the sample, or both;
(c) recording the signal amplitudes from the transverse relaxation ($T_2$) echo trains after incremental longitudinal relaxation ($T_1$) to produce a raw TD-NMR data set that emphasizes either faster relaxing components, slower relaxing components, or both, within the sample; and
(d) providing a computer which has been programmed to determine the amount of solids, fines and/or particles less than a given particle size in the sample by means of an optimized partial least squares chemometric model relating (i) the faster relaxing raw TD-NMR data sets obtained from a training set of oil sand process samples to the training samples' corresponding reference values obtained from analysis methods for determining bitumen, fine solids less than a given particle size, and/or the particle size distribution of the solids, and (ii) relating the slower relaxing raw TD-NMR data sets obtained from a training set of oil sand process samples to the training samples' corresponding reference values obtained from analysis methods for determining water and non-solids, and using the sample weight to determine the solids content by difference from the non-solids result.

In one embodiment, the first pulse sequence (FPS) of radio-frequency pulses is such that there are 15 transverse relaxation echoes spaced 0.4 ms apart, acquired at 28 $T_1$ points, exponentially spread from 5 ms through 200 ms, and the final stretch of $T_2$ measurement comprises 50 echoes spaced 2 ms apart, with 24 scans averaged together to improve the signal to noise ratio, resulting in the FPS measurement time of less than 1 minute.

In one embodiment, the second pulse sequence (SPS) of radio-frequency pulses is such that there are 200 transverse relaxation echoes spaced 0.6 ms apart, acquired at 11 $T_1$ points, exponentially spread from 5 ms through 20000 ms, and the final stretch of $T_2$ measurement comprises 200 echoes spaced 20 ms apart, with 4 scans averaged together to improve the signal to noise ratio, resulting in the SPS measurement time of less than 3 minutes.

In one embodiment, the diameter of the fine particles are <44 microns, <5.5 microns, and <1.9 microns. In another embodiment, the content of each particle size is a weight percentage of the whole sample. In another embodiment, the test sample is a tailings treatment process stream sample. In another embodiment, the test sample is a bitumen extraction process stream sample. In another embodiment, overall analysis time including test sample preheating is just over 1 hour.

DETAILED DESCRIPTION OF THE PREFERRED EMBODIMENTS

Figure 1:
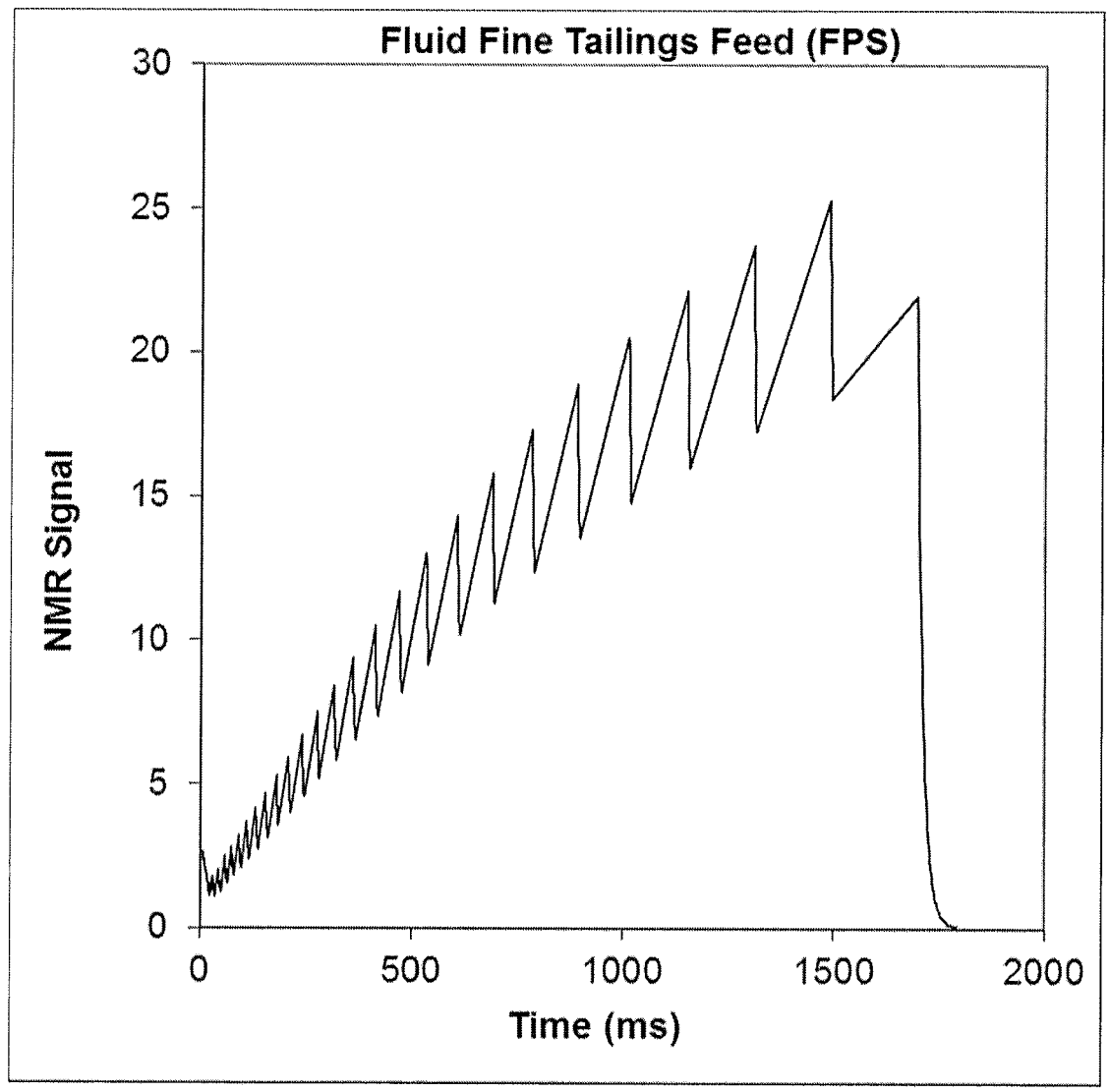
FIG. 1 shows the first pulse sequence (FPS) raw NMR signal for a fluid fine tailings centrifuge feed sample (~20% solids) plotted versus time.

The present invention uses low-field time-domain nuclear magnetic resonance (low-field TD-NMR) instruments to analyze various oil sands process streams to provide an accurate measurement of total solids and fine particles in addition to bitumen and water. Some significant advantages of using low-field TD-NMR measurements are that the measurements are quick, non-destructive, simple to use, and as a result, are less susceptible to technician bias. They typically require no solvents, gases, plumbing, or special ventilation, only electricity and a clean, temperature-controlled environment.

The present invention can be used with a variety of oil sands process streams, for example, oil sand slurry, extraction tailings including middlings and coarse tailings, fluid fine tailings (FFT) from settling basins, diluted FFT centrifuge feed, centrifuge cake, centrifuge centrate, and composite tailings feed and product streams.

In the examples that follow, low-field TD-NMR measurements were performed using a LF65 NMR instrument (Bruker BioSpin Ltd, Milton, ON, CAN). Two $T_1$-weighted $T_2$ measurement NMR pulse sequences performed in series were used to collect two separate groups of raw TD-NMR data sets. Partial least squares calibration models were created using the raw TD-NMR data sets from oil sands process streams having a known amount of solids, fine particles with diameters less than various sizes, bitumen, and water, (hereinafter referred to as "calibration samples"). The first $T_1$-weighted $T_2$ NMR pulse sequence measurement (FPS) was developed to emphasize the recording of the faster relaxing components within the sample (e.g. bitumen and water associated with fine particles). The second $T_1$-weighted $T_2$ NMR pulse sequence measurement (SPS) was developed to emphasize the recording of slower relaxing components in the sample (e.g. bulk water). For every calibration sample analyzed, both pulse sequences were automatically applied and the raw data stored as separate files. It was discovered that the combined use of the two different pulse sequences allows for more accurate predictions of the composition of oil sand process stream samples as compared to using a single pulse sequence. This is especially true when measuring both the solids content and fine particle content of samples that vary over a wide range of compositions (e.g. 2% versus 60% solids). Thus, the approach taken in the present invention allows for both fast and accurate measurements that were previously not possible.

EXAMPLE 1

In total, 206 oil sands process stream samples were used in this example. Two-thirds of the samples were used to construct the partial least squares (PLS) calibration models (i.e., calibration samples) and the resulting models were used to predict the composition of the remaining ⅓ of the samples (hereinafter referred to as the "test samples"). The oil sands process streams collected were predominantly from a centrifuge commercial demonstration plant used to centrifuge flocculant-treated oil sands tailings. However, to provide some additional sample diversity (including diversity of the minerals and particle size distribution), a number of other oil sands process streams were collected from various oil sands extraction plants. A few pure bitumen samples were also used to better differentiate between the NMR signal due to bitumen and the NMR signal due to water associated with fine particles. The samples were collected in either glass jars with plastic lids or high density polyethylene plastic bottles up to 250 mL in size. Using the same containers for the calibration samples and test set samples produced the most accurate results.

Prior to measurement in the LF65 NMR instrument, the samples were heated to 37° C. for at least 1 hour in a FREAS 625S convection oven (Thermo Fisher Scientific, Waltham, Mass., USA) to match the internal NMR probe temperature. Minimum sample heating times should be determined for a given oven and starting sample temperature. Sample weight and container material may also impact the minimum sample heating time. Once the sample was removed from the oven, it was quickly shaken by hand to briefly re-suspend any settled solids and then manually placed into the LF65 NMR probe cavity. Following the ~4 minute NMR analysis time, the sample was removed, and the process repeated for the next sample.

Figure 2:
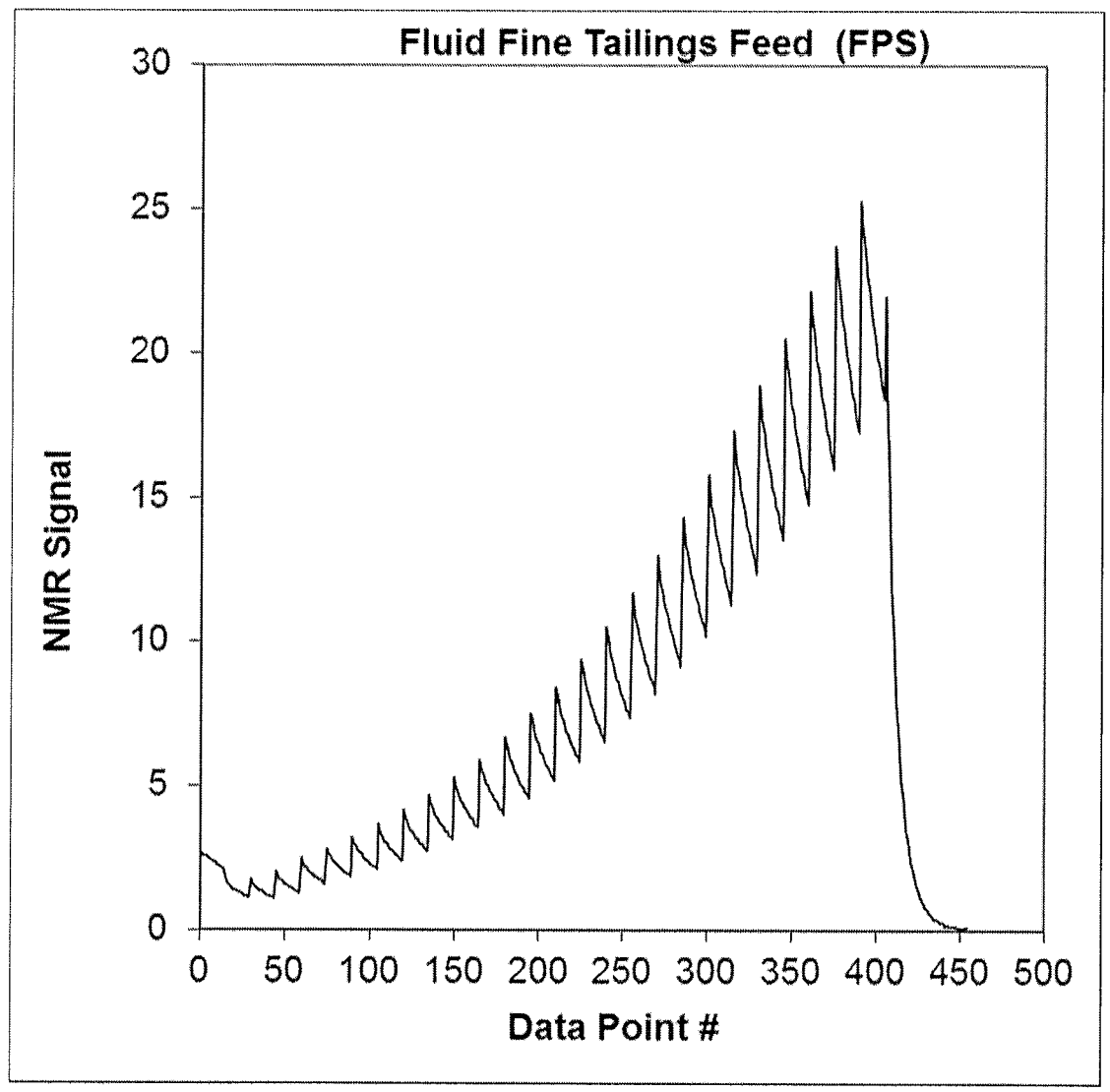
FIG. 2 shows the same data shown in FIG. 1 plotted versus data point number.
Figure 3:
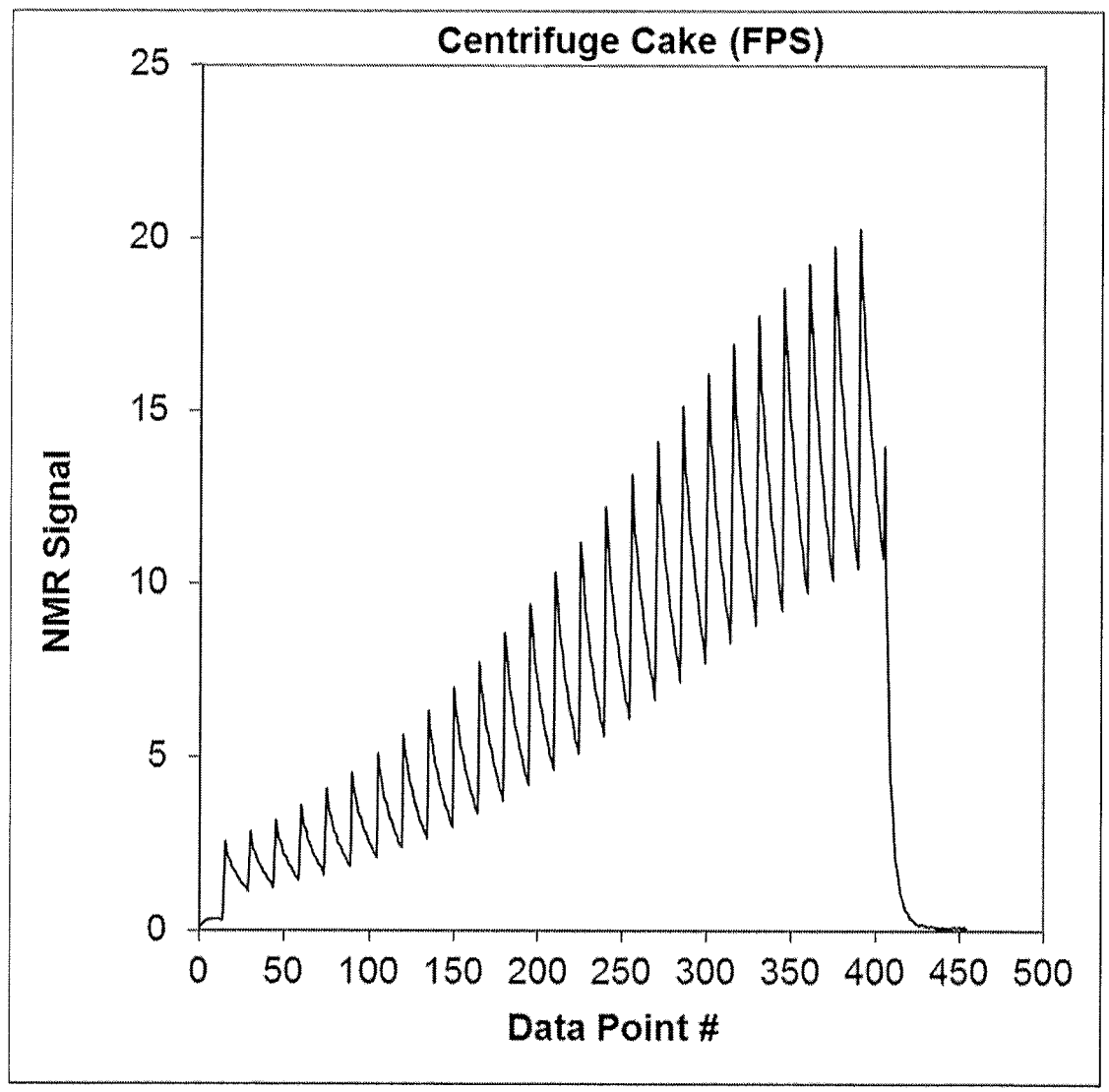
FIG. 3 shows the FPS raw NMR signal for a centrifuge cake sample (~50% solids).
Figure 4:
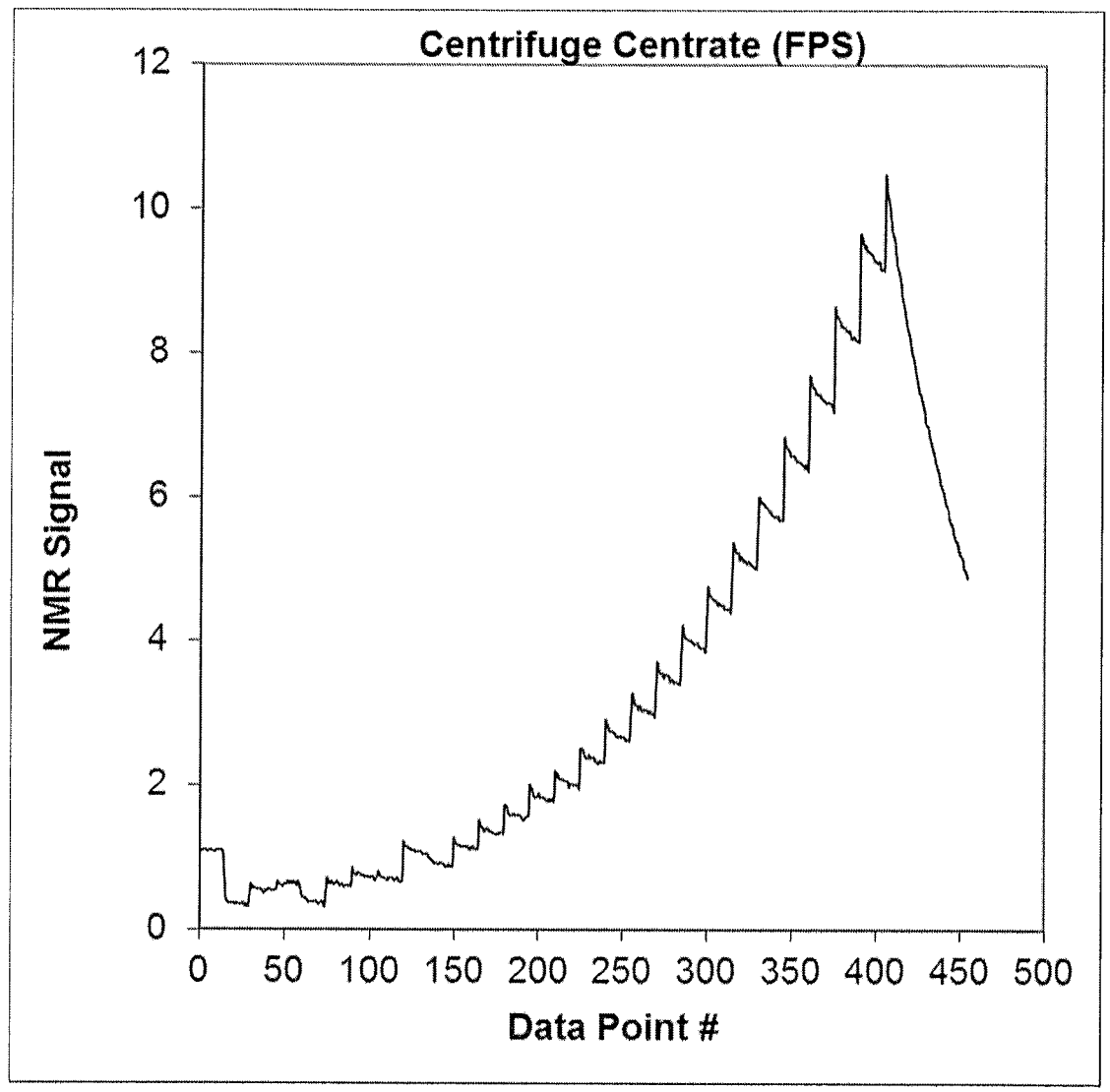
FIG. 4 shows the FPS raw NMR signal for a centrifuge centrate sample (~2% solids).
Figure 5:
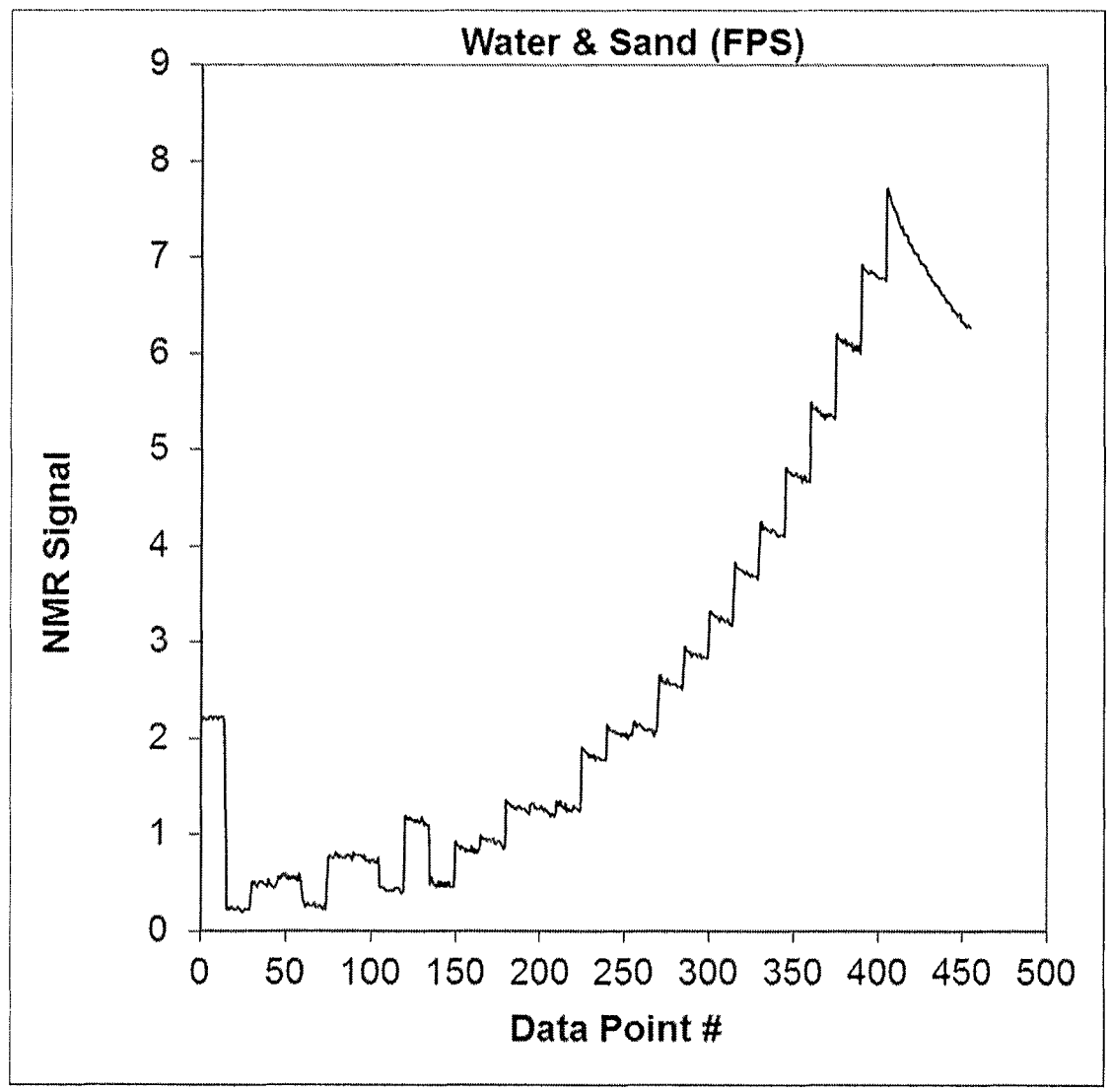
FIG. 5 shows the FPS signal for a mixture of coarse tailings sand and process water (~50% solids).
Figure 6:
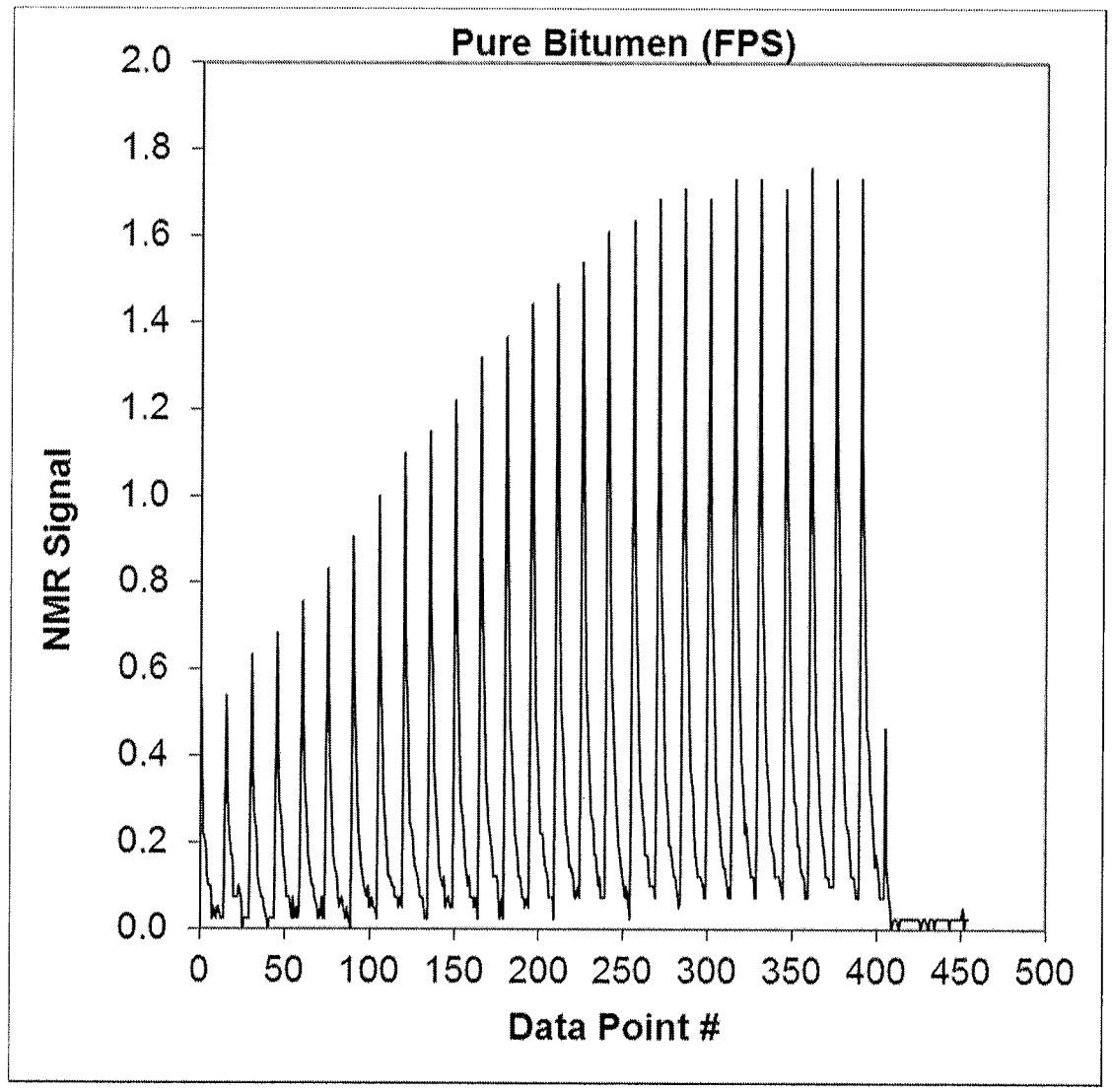
FIG. 6 shows the FPS raw NMR signal for pure bitumen.

FIG. 1 shows the first pulse sequence (FPS) raw NMR signal for a fluid fine tailings centrifuge feed sample (~20% solids) plotted versus time. FIG. 2 shows the same data plotted versus data point number, which makes it easier to visualize the data. FIG. 3 shows the FPS raw NMR signal for a centrifuge cake sample (~50% solids). FIG. 4 shows the FPS raw NMR signal for a centrifuge centrate sample (~2% solids). FIG. 5 shows the FPS signal for a mixture of coarse tailings sand and process water (~50% solids). The fastest $T_1$ weighted $T_2$ relaxation behavior is observed for the centrifuge cake sample (largest ratio of fine particles to water). The slowest relaxation behavior is observed for the coarse tailings sand and process water sample (smallest ratio of fine particles to water). FIG. 6 shows the FPS raw NMR signal for pure bitumen, which undergoes very fast relaxation.

The differences in the $T_1$ and $T_2$ relaxation behavior as measured by the FPS parameters between bitumen and water associated with solids of different particle sizes, mineral compositions (e.g. quartz, various clays), and at different ratios of solids-to-water, can be exploited using chemometrics to measure different components of interest that are associated with relatively fast relaxation, such as the concentration of fine particles in the sample <44 microns, <5.5 microns, <1.9 micron, and % bitumen.

Figure 7:
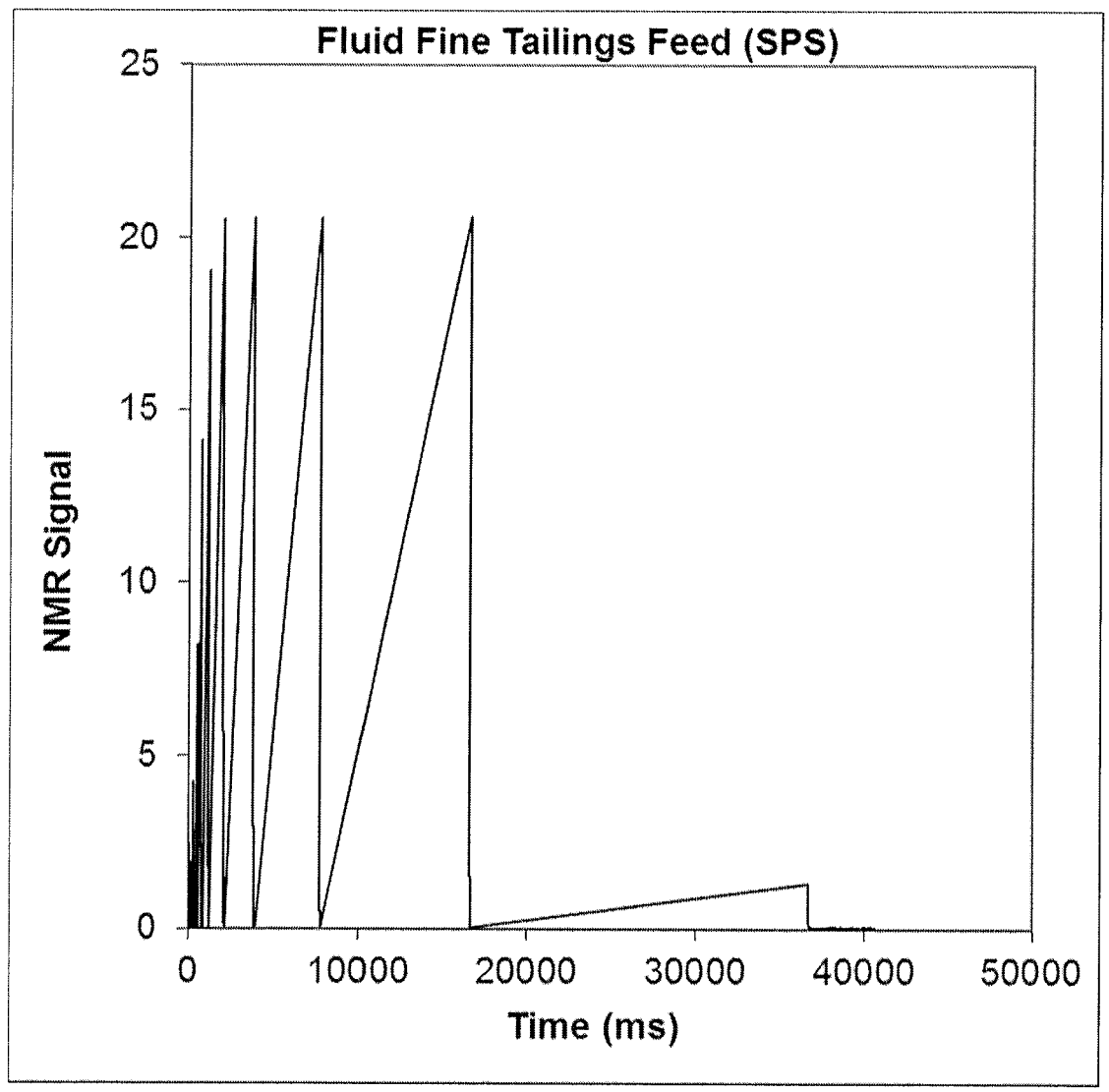
FIG. 7 shows the second pulse sequence (SPS) raw NMR signal for a fluid fine tailings centrifuge feed sample plotted versus time.
Figure 8:
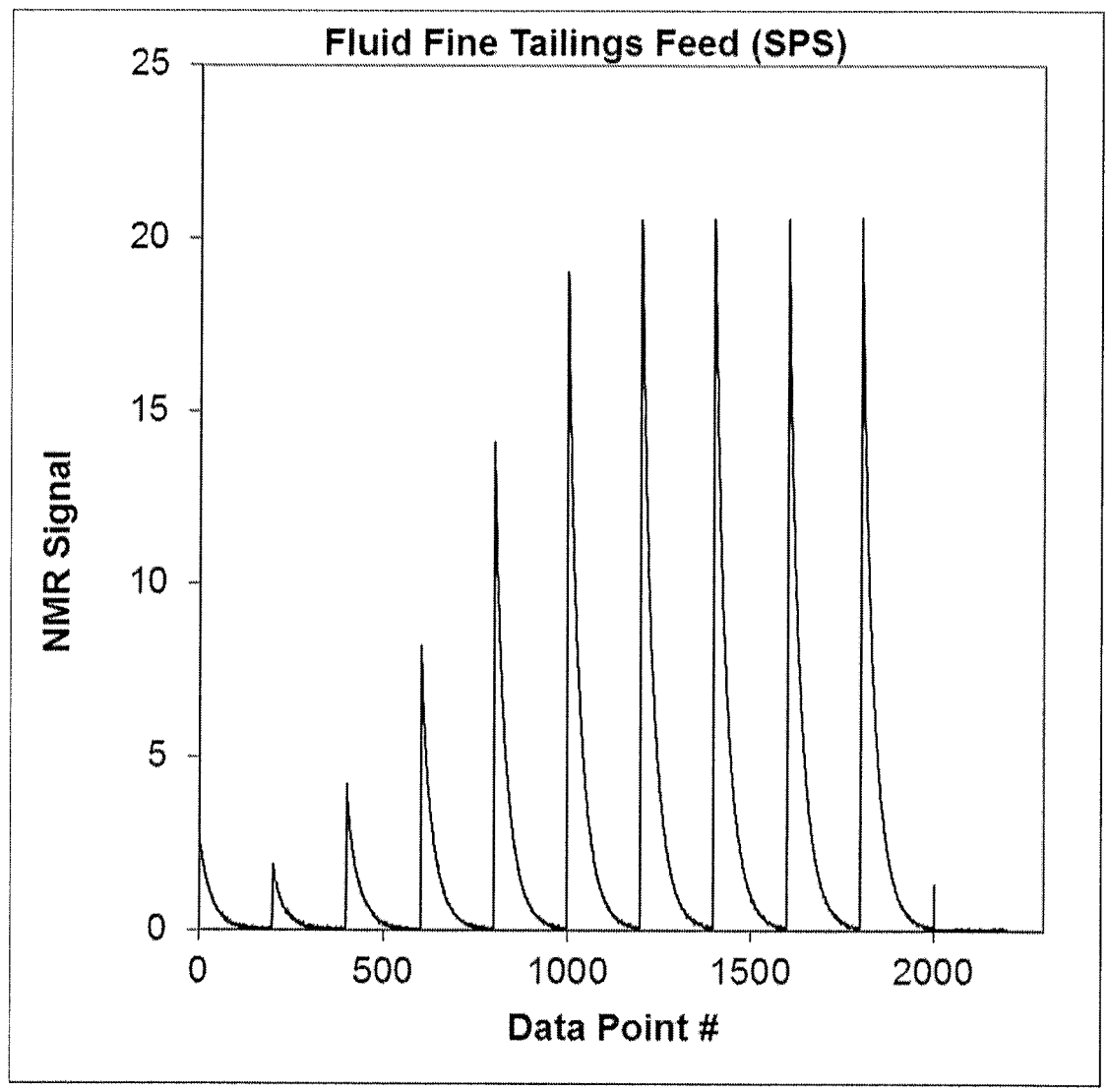
FIG. 8 shows the same data shown in FIG. 7 plotted versus data point number.
Figure 9:
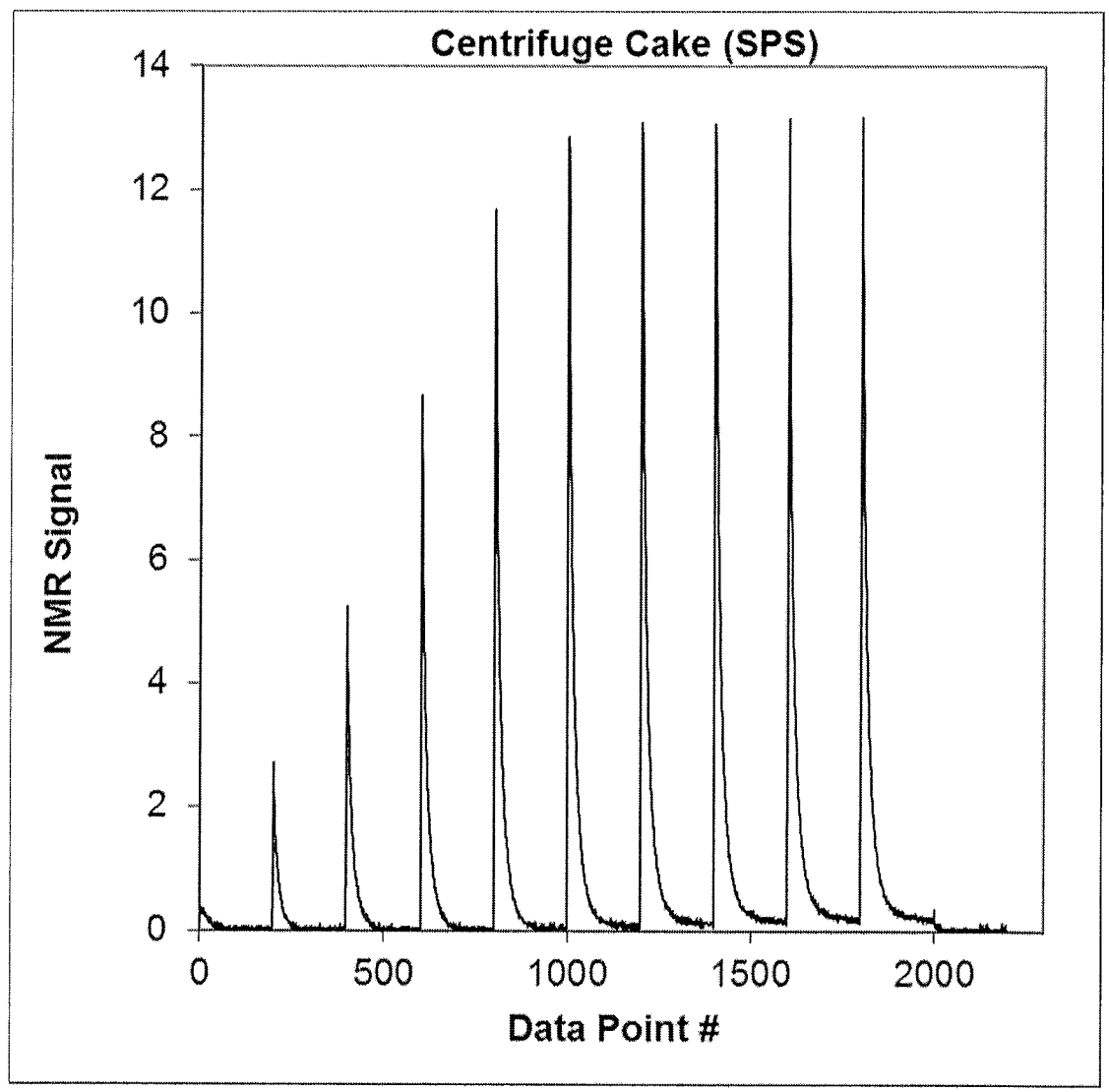
FIG. 9 shows the SPS raw NMR signal for a centrifuge cake sample.
Figure 10:
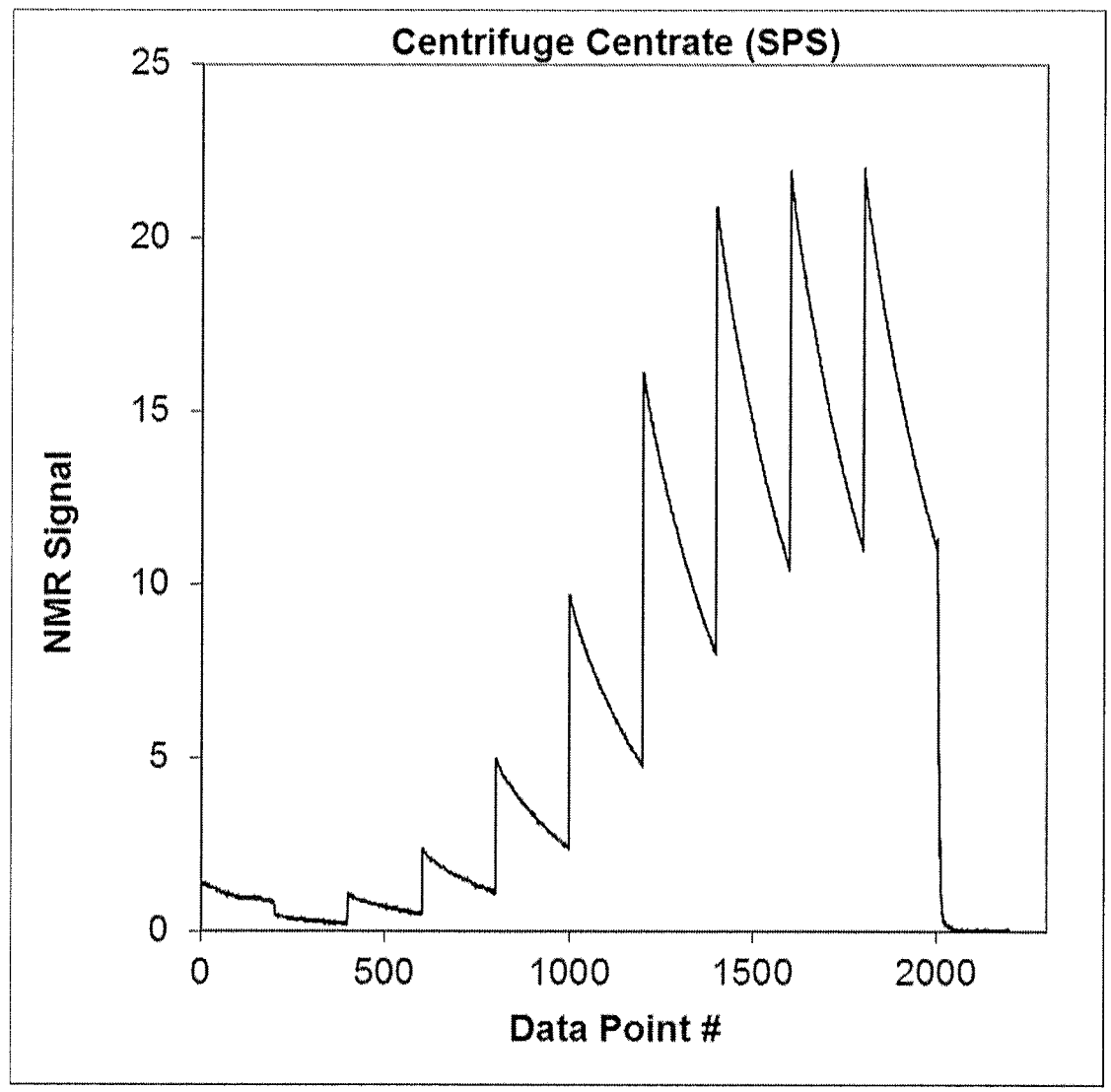
FIG. 10 shows the SPS raw NMR signal for a centrifuge centrate sample.
Figure 11:
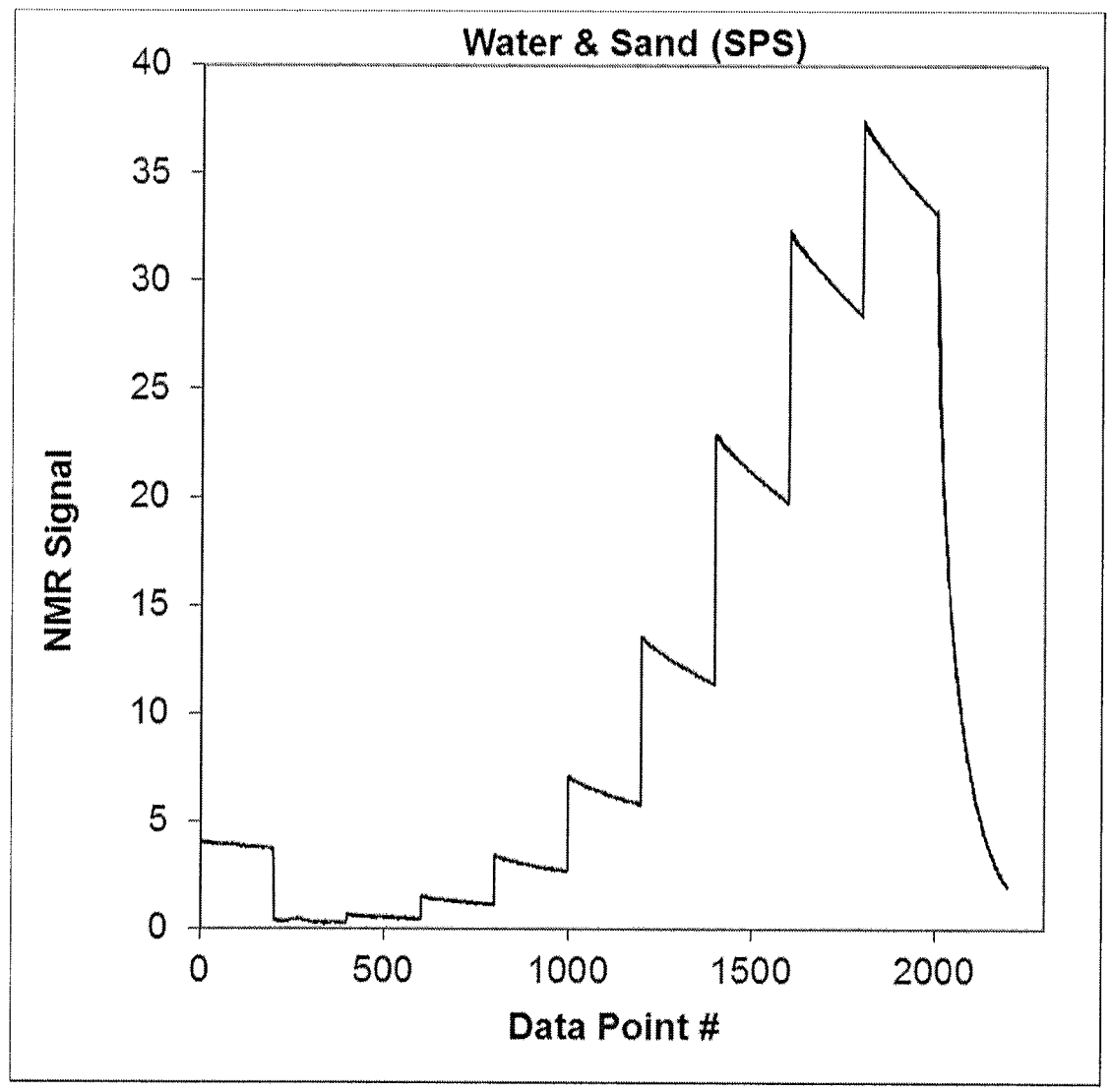
FIG. 11 shows the SPS raw NMR signal for a mixture of coarse tailings sand and process water.
Figure 12:
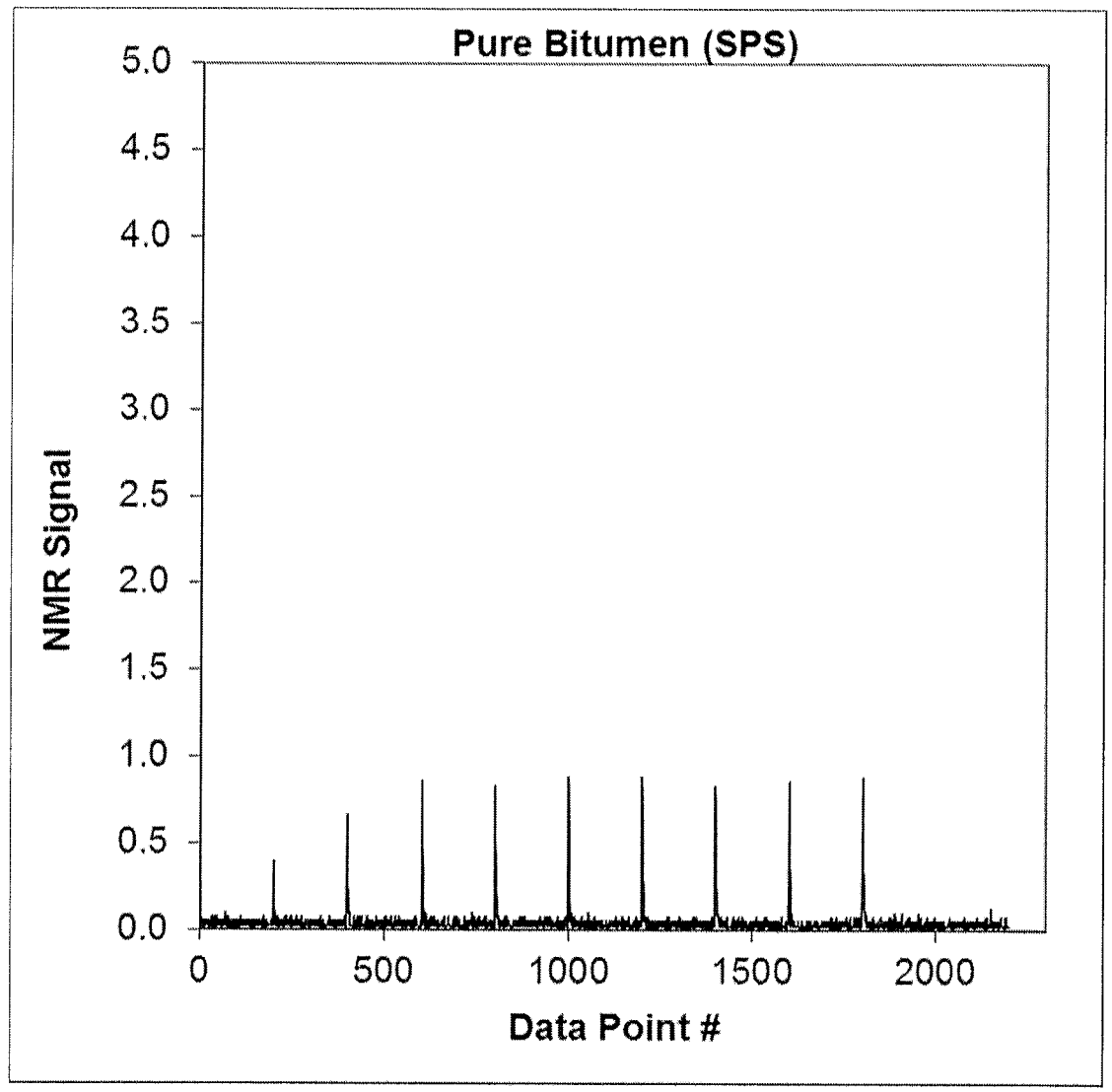
FIG. 12 shows the SPS raw NMR signal for pure bitumen.

FIG. 7 shows the second pulse sequence (SPS) raw NMR signal for a fluid fine tailings centrifuge feed sample plotted versus time. FIG. 8 shows the same data plotted versus data point number. FIG. 9 shows the SPS raw NMR signal for a centrifuge cake sample. FIG. 10 shows the SPS raw NMR signal for a centrifuge centrate sample. The SPS parameters have been selected to observe the relaxation behavior of slower relaxing components in the sample, such as water associated with smaller amounts of fine particles. FIG. 11 shows the SPS raw NMR signal for a mixture of coarse tailings sand and process water. FIG. 12 shows the SPS raw NMR signal for pure bitumen, which relaxes so quickly that only small amounts of signal are observed. However, sufficient bitumen signal is still collected under the SPS parameters to contribute to an accurate non-solids PLS calibration model.

Reference % bitumen, % water, and % solids results were provided by Dean-Stark extraction. Reference particle size information for the clean and dry solids produced by the Dean-Stark extraction was obtained by an LS 13 320 laser diffraction instrument (Beckman Coulter Inc., Brea, Calif., USA).

Chemometric reference results were calculated based on the grams of a component of interest in the sample container. Because the NMR produces minimal signal for solids, non-solids content reference values were used to develop a calibration that could accurately predict the solids content by difference. For example, a 100 grams tailings sample found to contain 30% solids, 68% water, and 2% bitumen by Dean & Stark (of whole sample), and 90% <44 micron, 50% <5.5 micron, and 20% <1.9 micron by Coulter laser diffraction (of solids fraction) would have reference values of (70% non-solids)×(100 g)=70 g non-solids; (68% water)×(100 g)=68 g water; (2% bitumen)×(100 g)=2 g bitumen; (90% <44 micron)×(30 g solids)=27 g<44 micron content; (50% <5.5 micron)×(30 g solids)=15 g<5.5 micron content; (20% <1.9 micron)×(30 g non-solids)=6 g<1.9 micron content. In the rare event that the NMR produces a slightly negative value as a test set prediction (e.g. −0.05% solids), a value of zero is returned instead.

Figure 13:
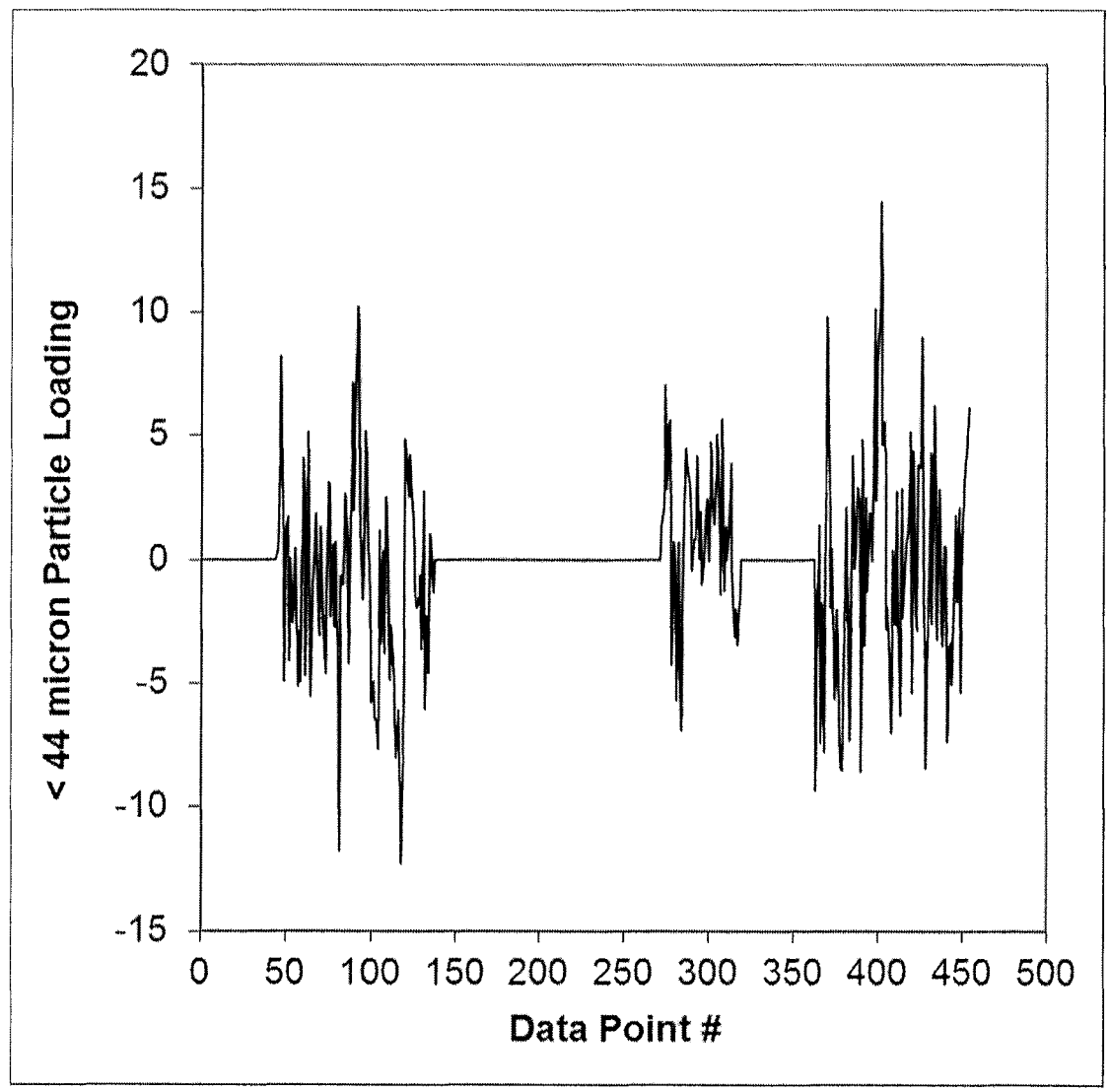
FIG. 13 shows the PLS model loading for determining the amount of fine particles (<44 micron) in the sample from the FPS raw NMR data.
Figure 14:
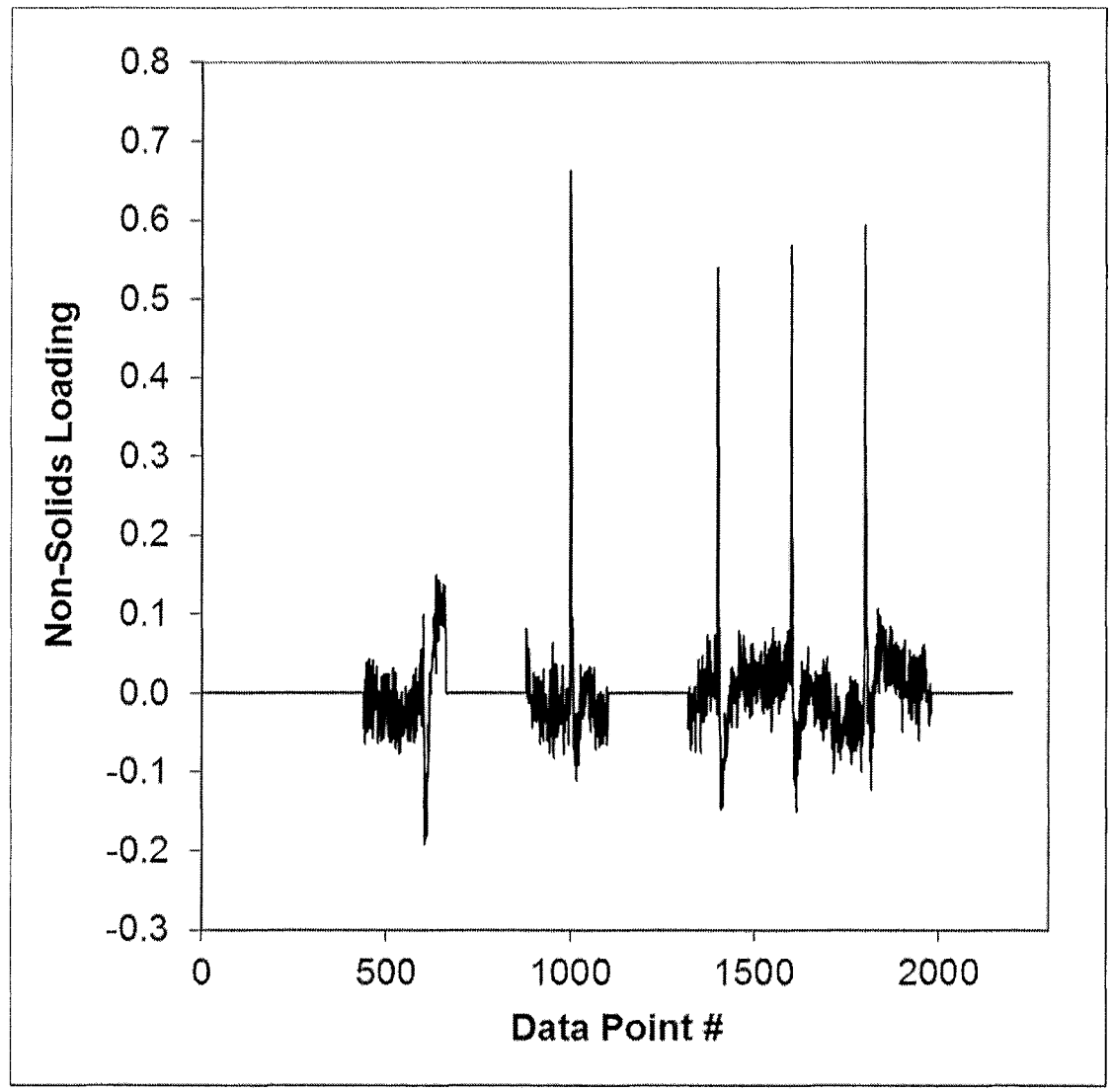
FIG. 14 shows the PLS model loading for determining the amount of non-solids in the sample from the SPS raw NMR data.

Separate chemometric PLS models for each component of interest were built using OPUS software version 7.0129 (Bruker BioSpin Ltd, Milton, ON, CAN). The regions of the raw NMR spectra that were used to build each PLS model were selected using the built-in optimization routine within the OPUS software. FIG. 13 shows the PLS model loading for determining the amount of fine particles (<44 micron) in the sample from the FPS raw NMR data. FIG. 14 shows the PLS model loading for determining the amount of non-solids in the sample from the SPS raw NMR data.

% Bitumen Content

Figure 15:
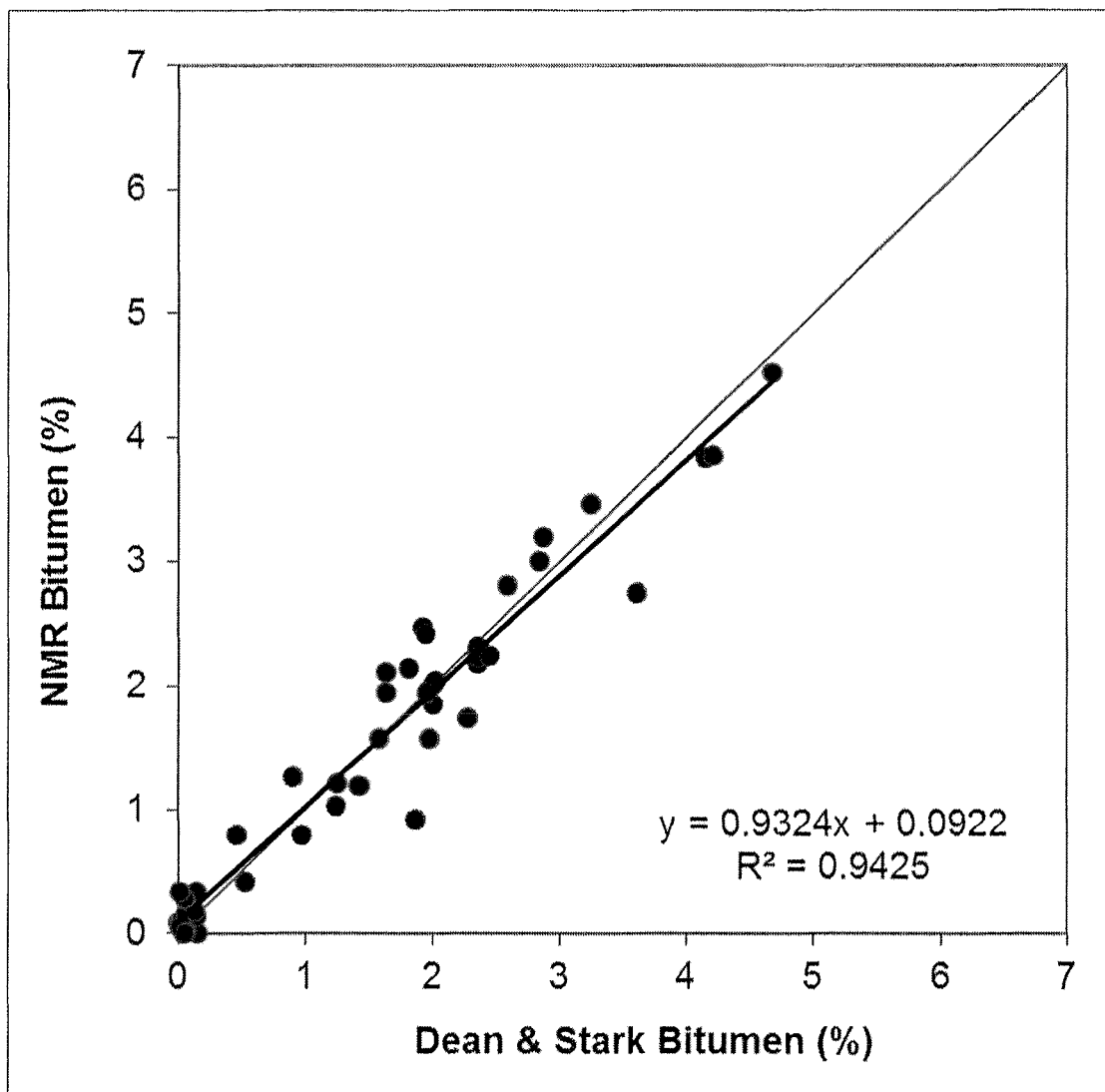
FIG. 15 shows the % bitumen agreement for test set samples measured by NMR using the first pulse sequence (FPS) compared to % bitumen measured by Dean & Stark.

FIG. 15 shows the % bitumen agreement for test set samples measured by NMR using the first pulse sequence (FPS) compared to % bitumen measured by Dean & Stark. Table 1 shows the average difference between the NMR and the Dean & Stark method, the standard deviation of the differences, the maximum absolute difference, as well as the R-squared value of the correlation. The average difference is very low, while the standard deviation of the differences, maximum difference, and R-squared value provide numeric indications of the magnitude of scatter.

TABLE 1

Average, standard deviation, maximum differences, and $R^2$ between the NMR first pulse sequence (FPS) bitumen model and the reference bitumen.

| Component | Average Difference NMR - Reference (% Absolute) | Std Dev of Difference (% Absolute) | Maximum Absolute Difference (% Absolute) | $R^2$ |
|---|---|---|---|---|
| % Bitumen (FPS model) | −0.01 | 0.31 | 0.94 | 0.9425 |

It should be noted that there was poorer agreement between % bitumen predicted using the second pulse sequence (SPS) bitumen PLS model and Dean & Stark. This is expected given that the second pulse sequence primarily collects NMR signal at long relaxation times, where the bitumen signal has largely already relaxed. This makes it difficult to differentiate the small amount of SPS bitumen signal from the overlapping water signal, which is why the FPS is much better for the measurement of bitumen.

% Water Content

Figure 16:
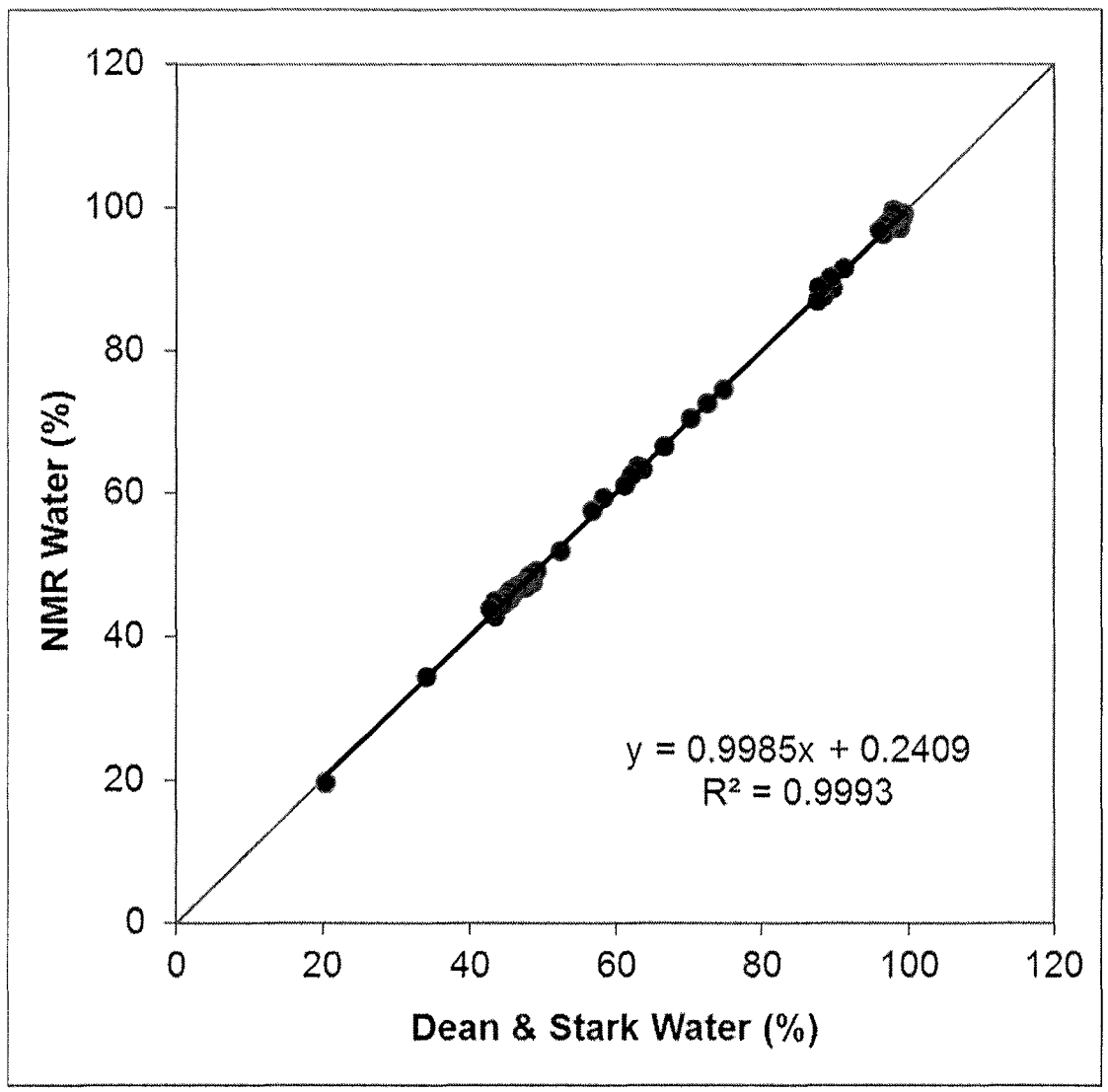
FIG. 16 shows the agreement with Dean & Stark measurements obtained for test set samples when % water is measured using the second pulse sequence (SPS).

FIG. 16 shows that excellent agreement with Dean & Stark measurements is obtained for test set samples when % water is measured using the second pulse sequence (SPS). Poorer agreement was obtained when the first pulse sequence (FPS) was used to measure the water content. This is also expected as the FPS does not collect enough signal at long relaxation times, where the water signal for samples with relatively few fines particles can be observed (e.g. centrate, coarse sand and water). Table 2 shows the same numeric indicators of the agreement for the % water measurements.

TABLE 2

Average, standard deviation, maximum differences, and $R^2$ between the NMR second pulse sequence (SPS) water model and the reference water.

| Component | Average Difference NMR - Reference (% Absolute) | Std Dev of Difference (% Absolute) | Maximum Absolute Difference (% Absolute) | $R^2$ |
|---|---|---|---|---|
| % Water (SPS model) | 0.14 | 0.64 | 1.8 | 0.9993 |

% Solids Content

Figure 17:
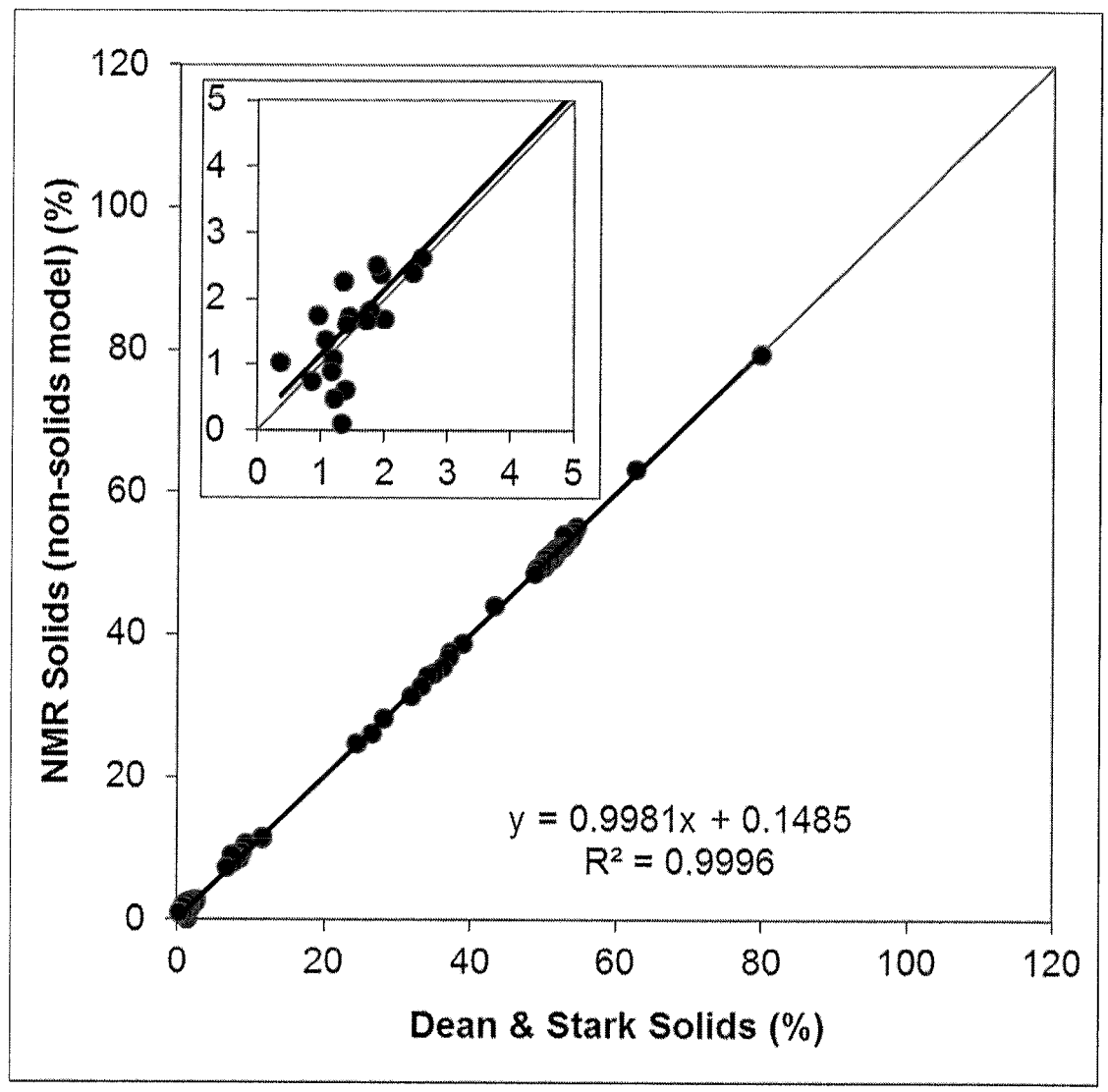
FIG. 17 shows the agreement obtained for test set samples between the % solids measured by the NMR based on the second pulse sequence (SPS) non-solids calibration model of the present invention and the reference % solids measured by Dean & Stark.
Figure 18:
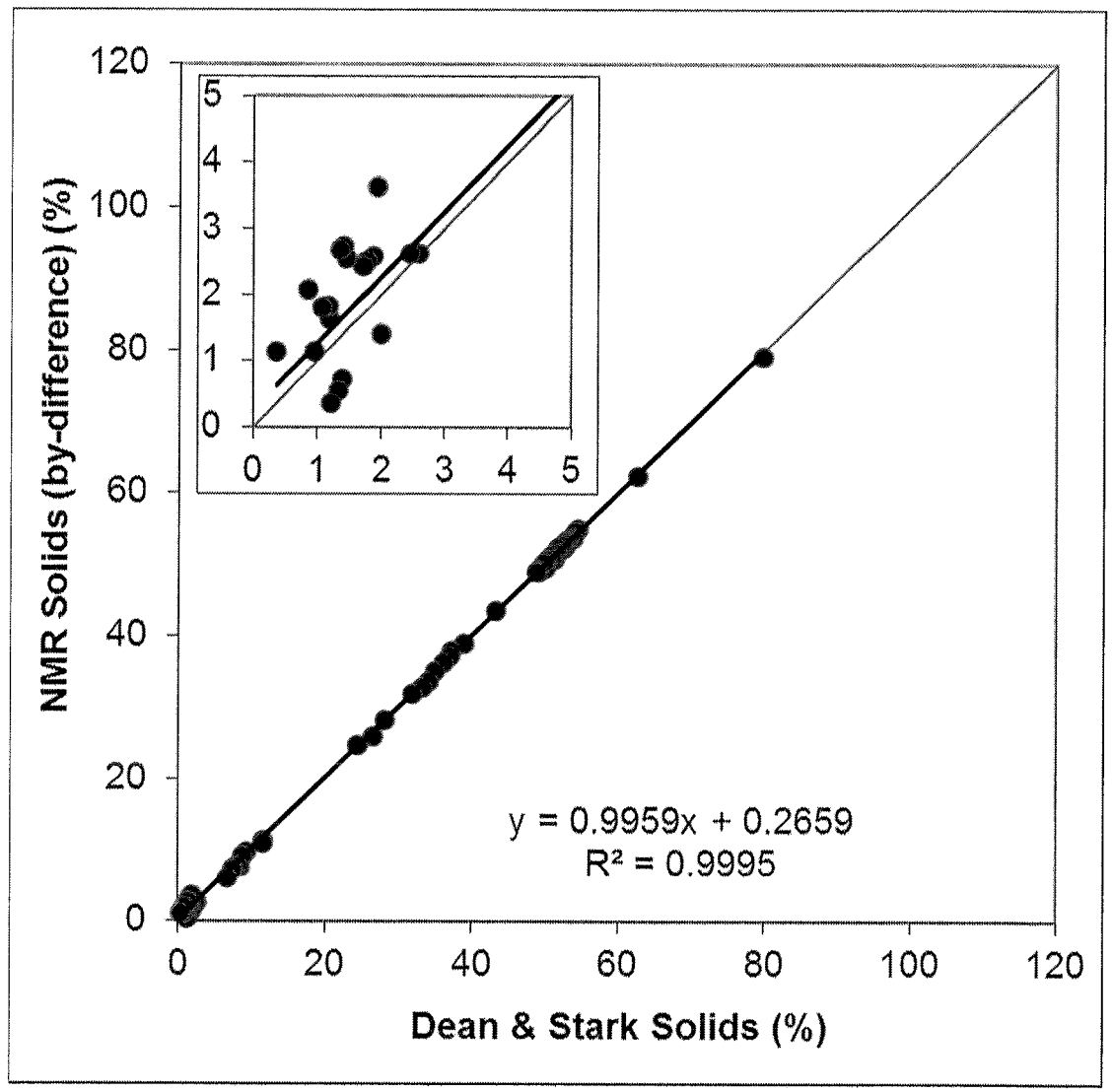
FIG. 18 shows that the agreement obtained by calculating the solids by difference (100%−% bitumen−% water).

FIG. 17 shows that excellent agreement is obtained for test set samples between the % solids measured by the NMR based on the second pulse sequence (SPS) non-solids calibration model of the present invention and the reference % solids measured by Dean & Stark. FIG. 18 shows that good agreement can also be obtained by calculating the solids by difference (100%−% bitumen−% water), although not as good as shown in FIG. 17 and not sufficiently good to measure the % solids in typical centrate samples shown in the magnified section of the graph. Table 3 shows how the SPS non-solids model % solids agreement with Dean-Stark compares to the by-difference % solids agreement with Dean-Stark based on a variety of numeric indicators.

TABLE 3

Average, standard deviation, maximum differences, and $R^2$ between the NMR solids content and the reference solids content.

| Component | Average Difference NMR - Reference (% Absolute) | Std Dev of Difference (% Absolute) | Maximum Absolute Difference (% Absolute) | $R^2$ |
|---|---|---|---|---|
| % Solids (non-solids SPS model) | 0.09 | 0.48 | 1.5 | 0.9996 |
| % Solids (100% - % bitumen by FPS - % water by SPS) | 0.14 | 0.51 | 1.7 | 0.9995 |

Amount of Fine Particles in the Sample

The amount of fine particles within the test samples are expressed as a percent of the entire sample (i.e. % <44 micron, % <5.5 micron, and % <1.9 micron of the sample), rather than as a percentage of the solids fraction. This is done because the amount of fine particles in the whole sample rather than as a percentage of the solids can be a more useful parameter for determining optimal process aid dosage and tracking fine particles.

For measuring the amount of fine particles in the sample, the first pulse sequence (FPS) models produced better agreement with the reference values compared to the second pulse sequence (SPS) models. This is because the FPS parameters emphasize the recording of the faster relaxing components, such as water associated with a relatively high amount of fine particles (e.g. FFT feed, centrifuge cake).

Figure 19:
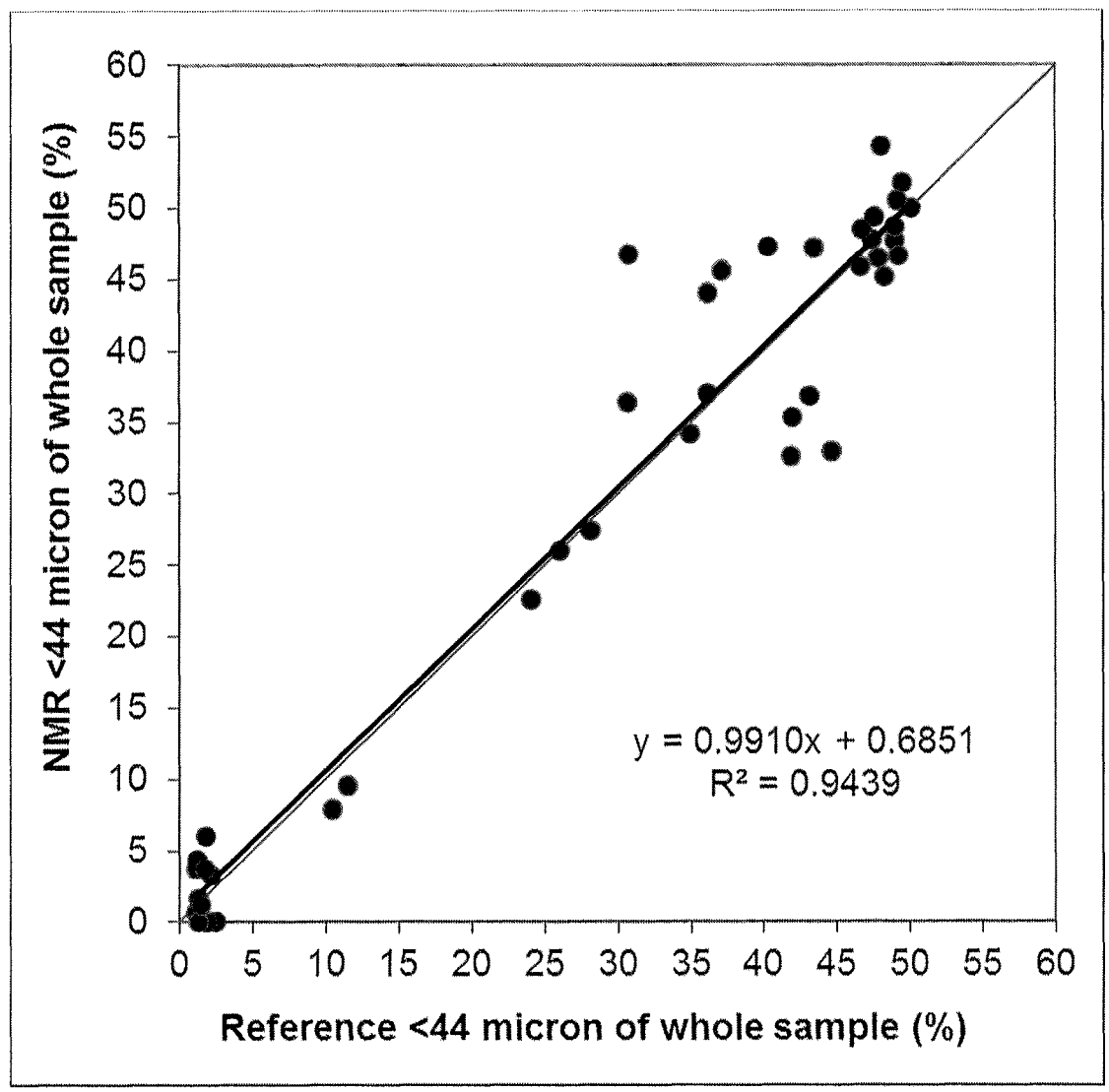
FIG. 19 shows the agreement for test set samples between the FPS model % <44 micron particles in the sample and the reference values.
Figure 20:
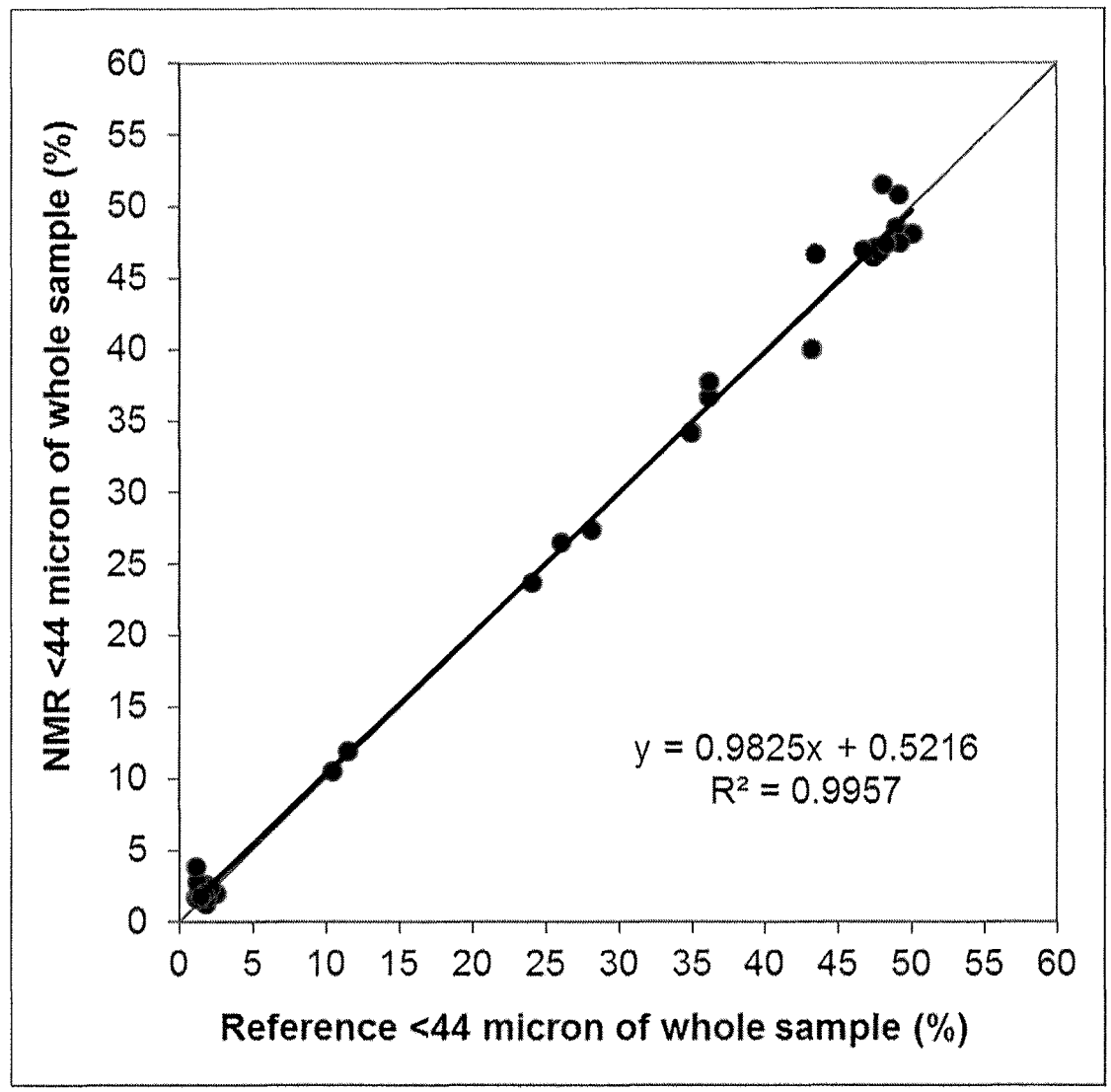
FIG. 20 shows the agreement of FIG. 19 when the samples with >2.5% bitumen are removed from both the calibration set and test set.

FIG. 19 shows the agreement for test set samples between the FPS model % <44 micron particles in the sample and the reference values. The agreement shows good average agreement with some scatter. Some of the scatter is partly due to the signal overlap between bitumen and water associated with high amounts of very fine particles. FIG. 20 shows how the agreement improves once the samples with >2.5% bitumen are removed from both the calibration set and test set. Table 4 shows the numerical indicators of the agreement for the % <44 micron particle content based on the FPS models,

TABLE 4

Average, standard deviation, maximum differences, and $R^2$ between the NMR first pulse sequence (FPS) % <44 micron particle content in the sample and the reference results.

| Component | Average Difference NMR - Reference (% Absolute) | Std Dev of Difference (% Absolute) | Maximum Absolute Difference (% Absolute) | $R^2$ |
|---|---|---|---|---|
| % <44 micron (FPS model) | 0.43 | 4.8 | 16.0 | 0.9439 |
| % <44 micron (FPS model with <2.5% bitumen calibration and test set samples only) | 0.06 | 1.4 | 3.5 | 0.9957 |

Figure 21:
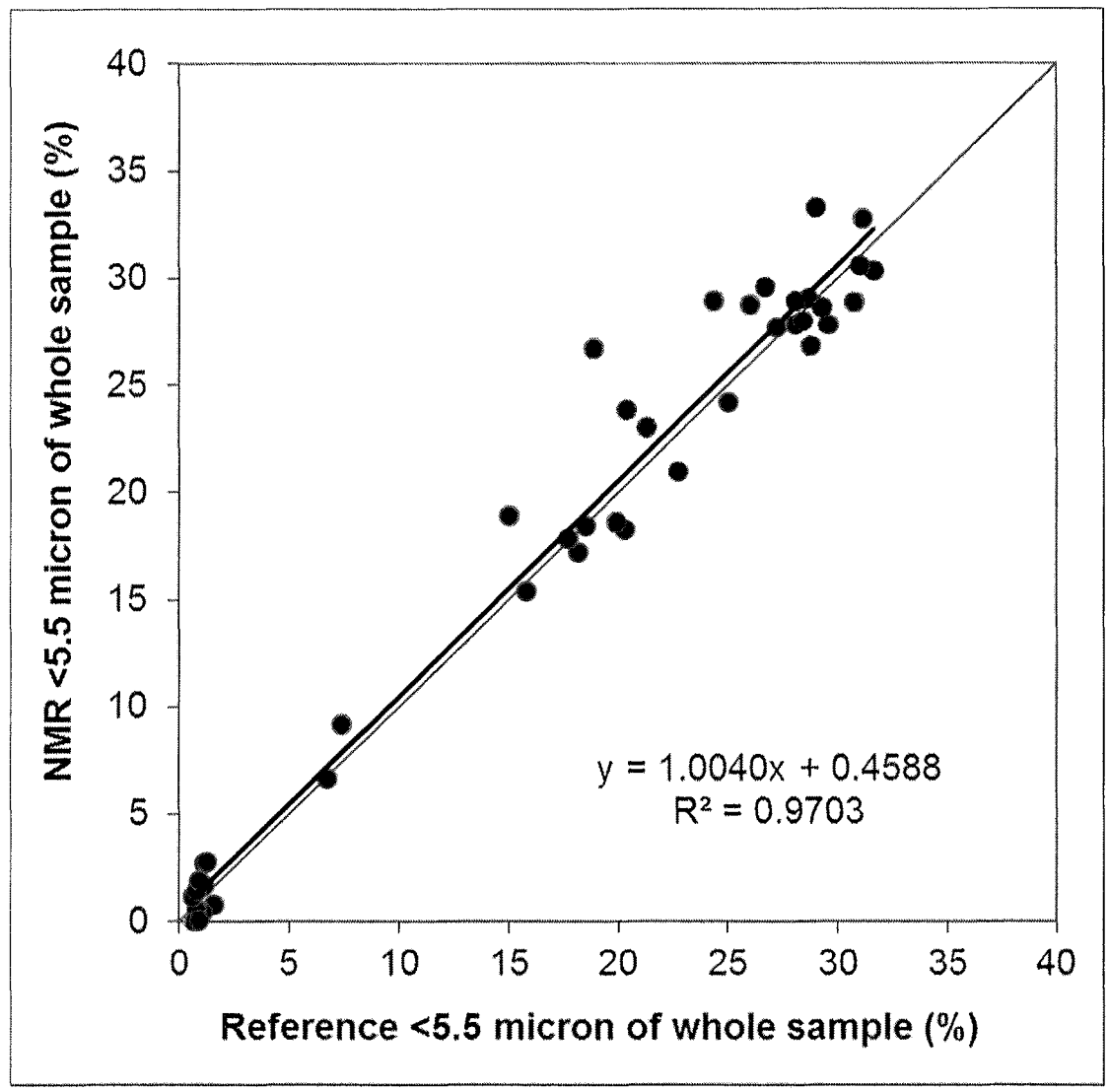
FIG. 21 shows the agreement for the % <5.5 micron particles content using the FPS model.
Figure 22:
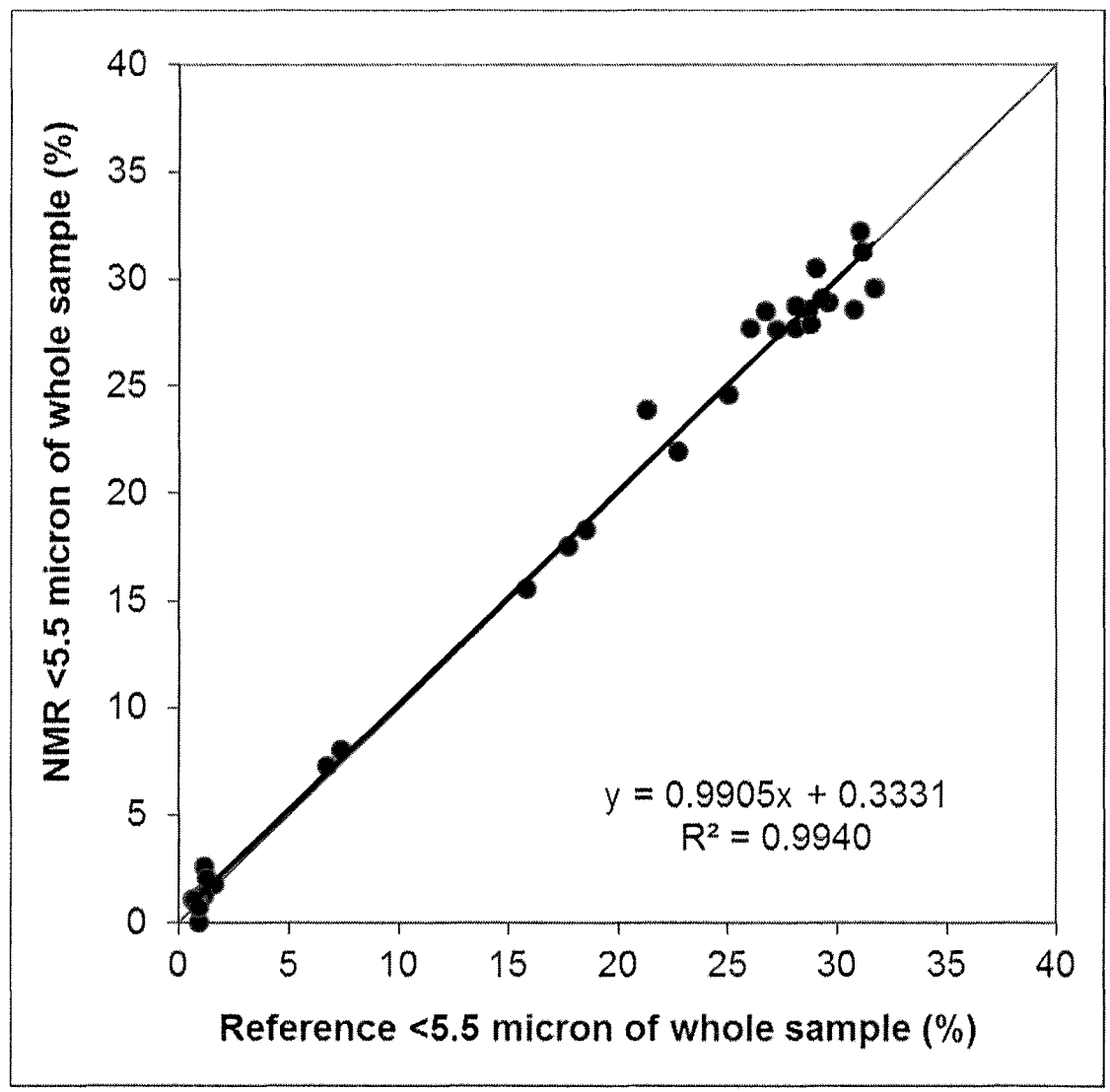
FIG. 22 shows the agreement of FIG. 21 when the samples with >2.5% bitumen are removed from the calibration set and test set.

FIG. 21 shows the agreement for the % <5.5 micron particles content using the FPS model, while FIG. 22 shows the same agreement, except with all of the samples with >2.5% bitumen removed from the calibration set and test set. Again, the removal of the high bitumen samples greatly improves the agreement. Table 5 shows the numerical indicators of the agreement for the % <5.5 micron particle content based on the FPS models.

TABLE 5

Average, standard deviation, maximum differences, and $R^2$ between the NMR first pulse sequence (FPS) % <5.5 micron particle content in the sample and the reference results.

| Component | Average Difference NMR - Reference (% Absolute) | Std Dev of Difference (% Absolute) | Maximum Absolute Difference (% Absolute) | $R^2$ |
|---|---|---|---|---|
| % <5.5 micron (FPS model) | 0.53 | 2.1 | 7.8 | 0.9703 |
| % <5.5 micron (FPS model with <2.5% bitumen calibration and test set samples only) | 0.18 | 1.0 | 2.6 | 0.9940 |

Figure 23:
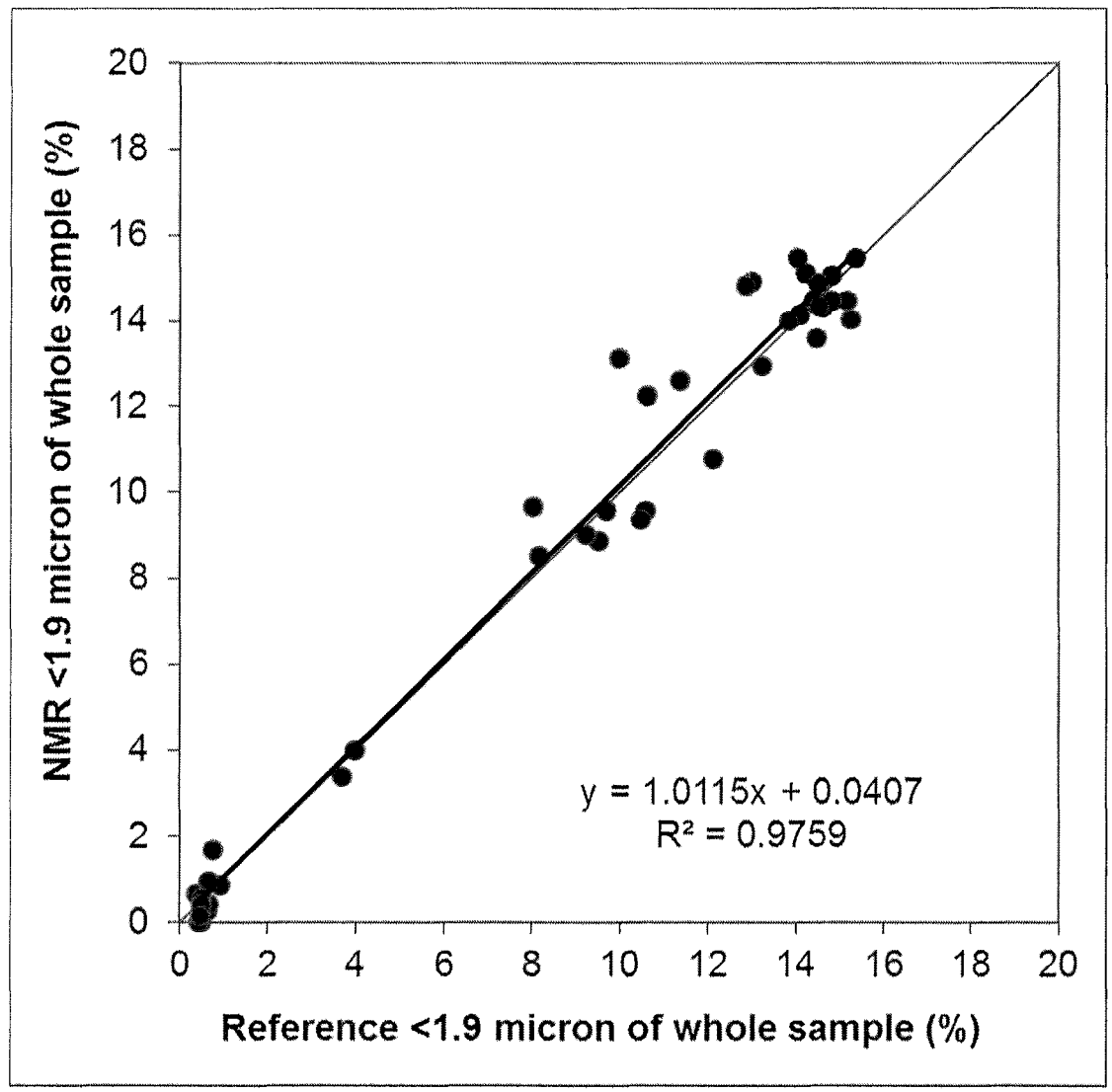
FIG. 23 shows the agreement for the % <1.9 micron particles content using the FPS model.
Figure 24:
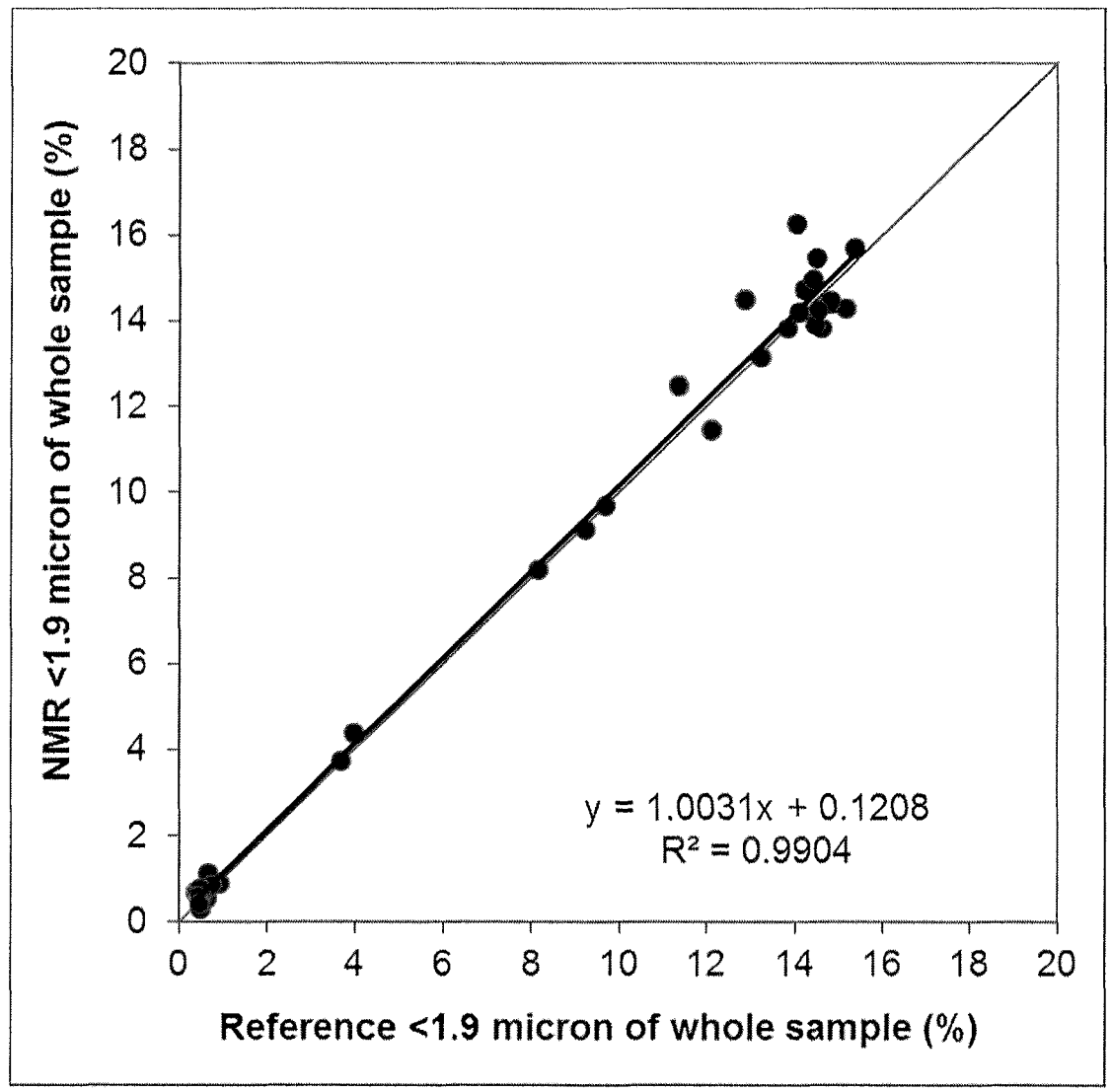
FIG. 24 shows the agreement of FIG. 23 when the samples with >2.5% bitumen are removed from the calibration set and test set.

FIG. 23 shows the agreement for the % <1.9 micron particles content using the FPS model, while FIG. 24 shows the same agreement, except with all of the samples with >2.5% bitumen removed from the calibration set and test set. Again, the removal of the high bitumen samples greatly improves the agreement. Table 6 shows the numerical indicators of the agreement for the % <1.9 micron particle content based on the FPS models.

TABLE 6

Average, standard deviation, maximum differences, and $R^2$ between the NMR first pulse sequence (FPS) % <1.9 micron particle content in the sample and the reference results.

| Component | Average Difference NMR - Reference (% Absolute) | Std Dev of Difference (% Absolute) | Maximum Absolute Difference (% Absolute) | $R^2$ |
|---|---|---|---|---|
| % <1.9 micron (FPS model) | 0.14 | 0.94 | 3.1 | 0.9759 |
| % <1.9 micron (FPS model with <2.5% bitumen calibration and test set samples only) | 0.15 | 0.63 | 2.2 | 0.9904 |

Thus, the ability of the NMR to predict the amount of fine particles in the sample at various particle sizes in just over a 1 hour turnaround time (sample heating time is 1 hour and the NMR analysis time is ~4 minutes) has been demonstrated.

EXAMPLE 2

Three centrifuged tailings samples (FFT feed, centrate, and centrifuge cake) were analyzed 5 times each by one lab technician and then another 5 times each by a different lab technician to determine if differences in the way the samples are shaken by hand and introduced into the NMR instrument affects the results. Table 7 shows the results of this repeatability test. Overall, both the repeatability and agreement between the two sets of results produced by the different lab technicians are excellent.

Due to the scatter in the agreement in the % fines prediction (for example, see FIG. 19), the NMR can sometimes predict that there are slightly higher % >44 micron fines content in the sample, than there are total % solids. This was observed for an FFT feed sample (e.g. % solids of 25.2% versus % <44 micron fines content of 27.2%). Since the agreement with the reference method is much better for the % solids measurement compared to the fine particle measurements, one way to deal with this discrepancy is to automatically report the % <44 micron particle content as being equal to the % solids when this situation occurs.

TABLE 7

Repeatability of 3 centrifuged tailings samples analyzed times 5 each by 2 different Lab Technicians. Note that the % Bitumen, % Water, and % Solids (non-solids model) results were normalized to add to 100%. The % < 44, % < 5.5, and % < 1.9 results are based on the entire sample weight.

| | Centrate Sample Average (% Absolute) | Centrate Sample Std Dev (% Absolute) | FFT Feed Sample Average (% Absolute) | FFT Feed Sample Std Dev (% Absolute) | Cake Sample Average (% Absolute) | Cake Sample Std Dev (% Absolute) |
|---|---|---|---|---|---|---|
| % Bitumen (Tech #1) | 0.77 | 0.13 | 1.61 | 0.03 | 2.68 | 0.05 |

TABLE 7-continued

Repeatability of 3 centrifuged tailings samples analyzed times 5 each by 2 different Lab Technicians. Note that the % Bitumen, % Water, and % Solids (non-solids model) results were normalized to add to 100%. The % < 44, % < 5.5, and % < 1.9 results are based on the entire sample weight.

| | Centrate Sample Average (% Absolute) | Centrate Sample Std Dev (% Absolute) | FFT Feed Sample Average (% Absolute) | FFT Feed Sample Std Dev (% Absolute) | Cake Sample Average (% Absolute) | Cake Sample Std Dev (% Absolute) |
|---|---|---|---|---|---|---|
| % Bitumen (Tech #2) | 0.92 | 0.23 | 1.60 | 0.04 | 2.67 | 0.04 |
| % Water (Tech #1) | 94.50 | 0.18 | 73.12 | 0.20 | 46.50 | 0.12 |
| % Water (Tech #2) | 94.11 | 0.30 | 73.21 | 0.13 | 46.57 | 0.02 |
| % Solids (Tech #1) | 4.73 | 0.07 | 25.27 | 0.21 | 50.82 | 0.14 |
| % Solids (Tech #2) | 4.96 | 0.17 | 25.20 | 0.16 | 50.76 | 0.03 |
| % < 44 micron (Tech #1) | 4.04 | 0.13 | 27.17 | 0.45 | 43.16 | 0.11 |
| % < 44 micron (Tech #2) | 4.23 | 0.29 | 27.19 | 0.48 | 43.24 | 0.04 |
| % < 5.5 micron (Tech #1) | 2.06 | 0.08 | 17.94 | 0.20 | 23.29 | 0.05 |
| % < 5.5 micron (Tech #2) | 2.03 | 0.06 | 17.94 | 0.19 | 23.34 | 0.01 |
| % < 1.9 micron (Tech #1) | 0.99 | 0.12 | 8.54 | 0.06 | 14.11 | 0.03 |
| % < 1.9 micron (Tech #2) | 0.90 | 0.10 | 8.68 | 0.12 | 14.14 | 0.02 |

EXAMPLE 3

Other useful parameters of oil sand process samples can also be measured using the approach described herein, provided that the parameter being measured is strongly correlated to the surface area of the solids associated with water in the sample. The methylene blue index (MBI) titration method, based on ASTM C837-09 or one of several related procedures, is a commonly used measure of clay cation-exchange activity (often reported in units of MB milliequivalents per 100 g of clean and dry solids) that can be measured using a similar approach as described herein for measuring the amount of fine particles by TD-NMR.

In this case, the PLS calibration reference values should be calculated as the MB milliequivalents within the entire sample. This can be calculated by multiplying the MBI results for the calibration sample (e.g. in units of meq/100 g of clean and dry solids produced by Dean-Stark extraction) by the % solids by Dean-Stark extraction, and then multiplying by the sample weight to obtain a reference value in units of meq in the entire sample container. For example, the PLS calibration reference value for a sample with 12 MB meq/100 g dry solids, 20% solids, and a sample weight of 120 g would be (12 MB meq/100 g solids)×(20 g solids/100 g sample)×(120 g sample)=2.88 MB meq in the sample. A PLS model is then created using these reference values and the FPS raw NMR data for a set of calibration samples, followed by applying the built-in optimization routine with the OPUS software to select the most useful regions of the raw NMR spectra for measuring MBI values. The MBI PLS loading can then be used to determine the MB meq in an unknown test sample from its FPS raw NMR data. Using the % solids determined by the non-solids NMR model and the sample weight of the test sample, the MBI value can be reported in units of MB meq/100 g of dry solids.

Figure 25:
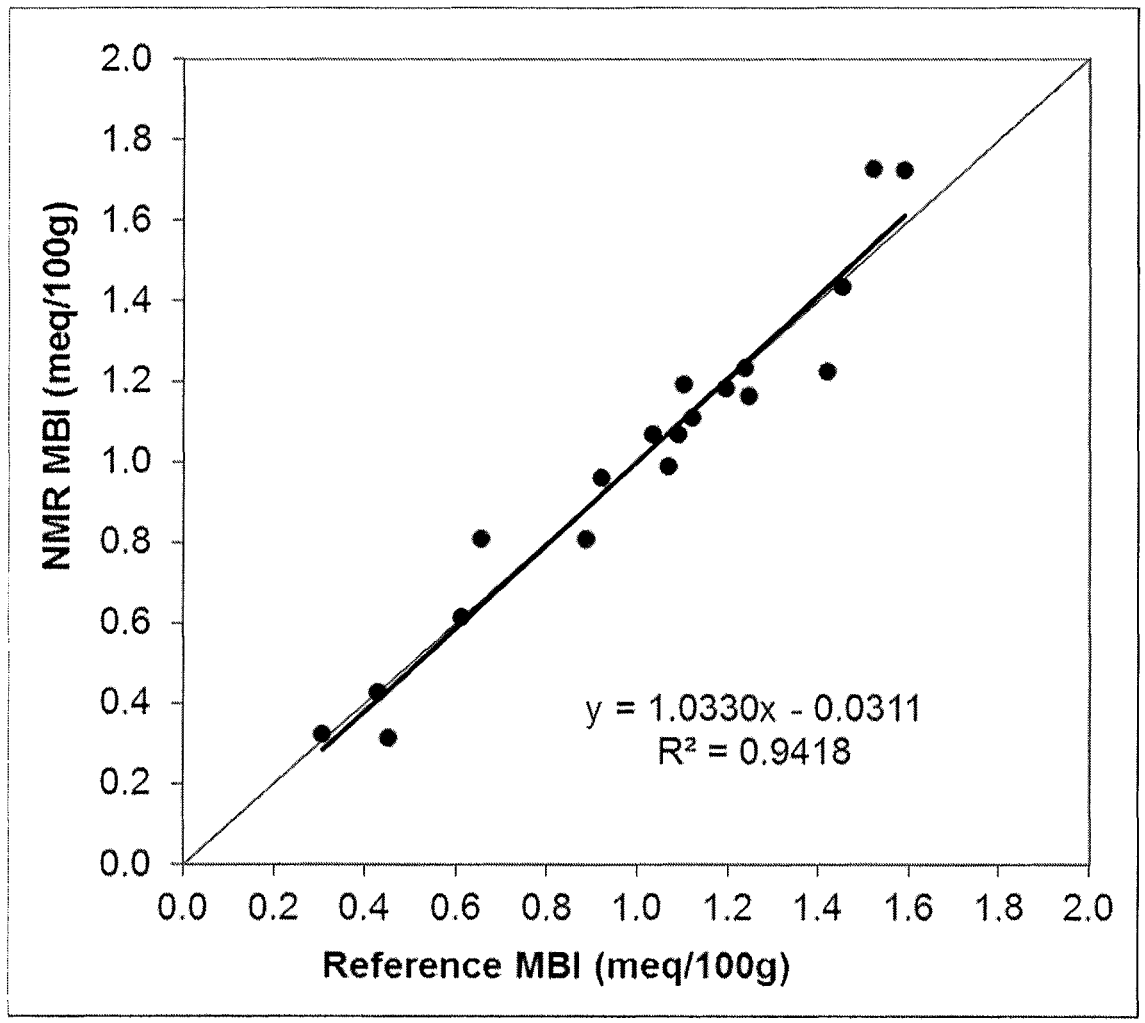
FIG. 25 shows the agreement for the Methylene Blue Index using a FPS model.
Figure 26:
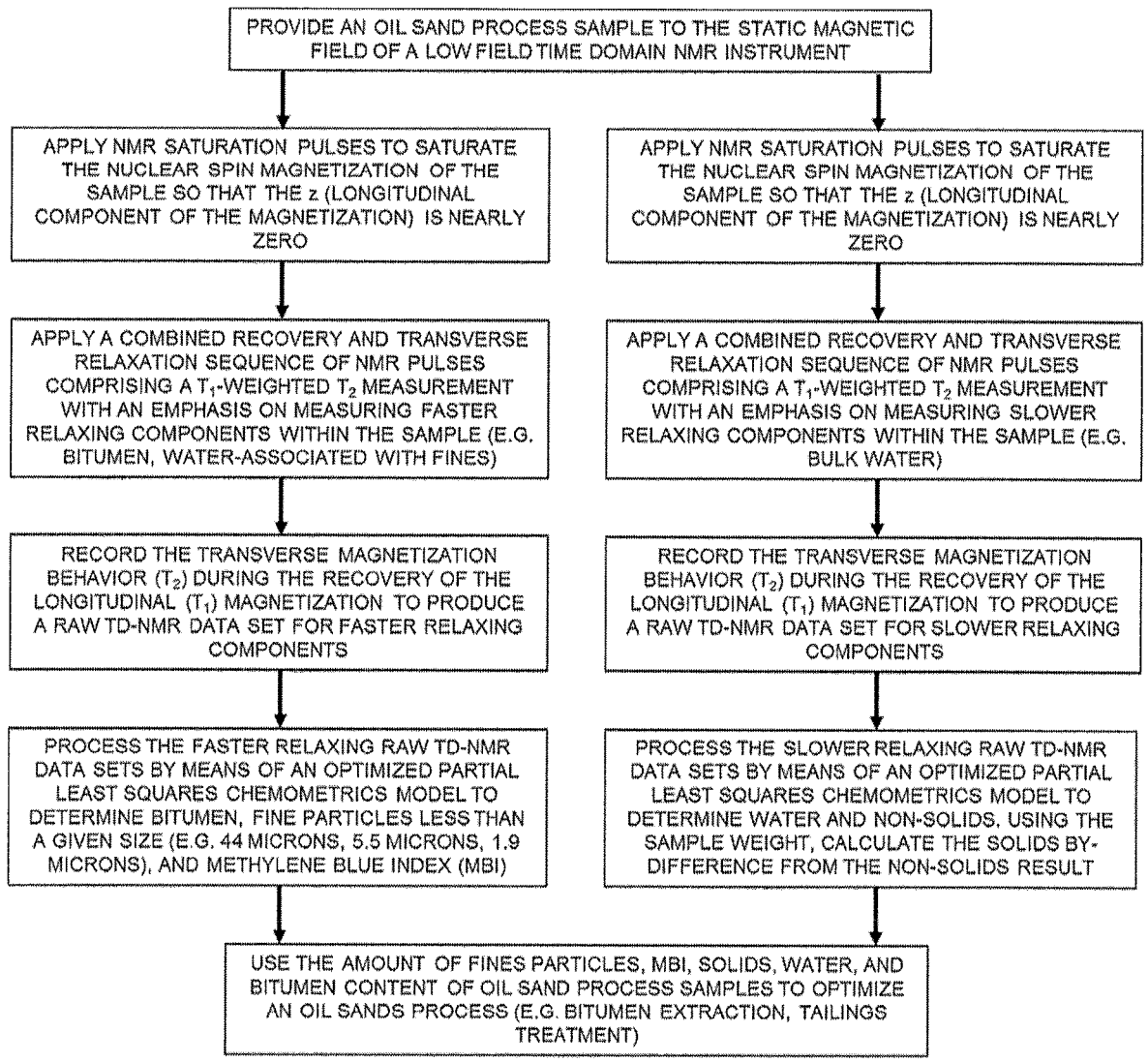
FIG. 26 shows a flow chart for one embodiment of the present invention.

This embodiment was demonstrated using 19 composite (non-segregating) tailings samples. These samples were analyzed by TD-NMR as described above to determine MBI (meq/100 g) using a FPS model and % solids using a non-solids SPS model. FIG. 25 shows the agreement for the cross validation MBI results on all 19 samples based on the FPS MBI model compared to the reference MBI values. Table 8 shows the numerical indicators of the agreement for the NMR MBI results compared with the reference values.

TABLE 8

Average, standard deviation, maximum differences, and $R^2$ between the NMR first pulse sequence (FPS) Methylene Blue Index in the sample and the reference results.

| Component | Average Difference NMR - Reference | Std Dev of Difference | Maximum Absolute Difference | $R^2$ |
|---|---|---|---|---|
| MBI (meq/100 g) | 0.003 | 0.10 | 0.21 | 0.9418 |

What is claimed:

1. A method for determining the solids content, fines content and/or particle size distribution in an oil sands process stream test sample comprising bitumen, solids and water using low-field time-domain NMR, comprising:
building partial least squares calibration models for non-solids content and fine particles content(s) less than a given, or multiple, particle size(s) using oil sands process streams calibration samples having a known bitumen, water, and solids contents, and a known particle size distribution of the solids, by subjecting the calibration samples to a first $T_1$-weighted $T_2$ NMR pulse sequence that measures fast relaxing signals and a second $T_1$-weighted $T_2$ NMR pulse sequence that measures slow relaxing signals, based on the shift to faster water signal relaxation times as the ratio of fine particles to water in the sample is increased;
subjecting the test sample to either the first fast relaxing $T_1$-weighted $T_2$ NMR pulse sequence, the second slow relaxing $T_1$-weighted $T_2$ NMR pulse sequence, or both, and measuring the produced signal amplitudes;

determining the fine particles content and/or particle size distribution in the test sample by applying the calibration loading(s) for fine particles less than a given, or multiple, particle size(s) to the fast relaxing pulse sequence raw NMR data; and/or determining the solids content by applying the non-solids loading to the slow relaxing pulse sequence raw NMR data and calculating the solids content by difference from the sample weight.

2. The method as claimed in claim 1, wherein the first $T_1$-weighted $T_2$ measurement NMR pulse sequence (FPS) is such that there are 15 transverse relaxation echoes spaced 0.4 ms apart, acquired at 28 $T_1$ points, exponentially spread from 5 ms through 200 ms, and the final stretch of $T_2$ measurement comprises 50 echoes spaced 2 ms apart, with 24 scans averaged together to improve the signal to noise ratio, resulting in the FPS measurement time of less than 1 minute and the second $T_1$-weighted $T_2$ measurement NMR pulse sequence (SPS) is such that there are 200 transverse relaxation echoes spaced 0.6 ms apart, acquired at 11 $T_1$ points, exponentially spread from 5 ms through 20000 ms, and the final stretch of $T_2$ measurement comprises 200 echoes spaced 20 ms apart, with 4 scans averaged together to improve the signal to noise ratio, resulting in the SPS measurement time of less than 3 minutes.

3. The method of claim 1, wherein the bitumen, solids and water contents of the oil sands process streams calibration samples are determined by Dean-Stark extraction.

4. The method of claim 1, wherein the particle size distribution of the oil sands process streams calibration samples are determined by laser diffraction or wet sieve.

5. The method as claimed in claim 1, wherein the test sample is an oil sands process sample or oil sands tailings treatment sample containing solids in the range of 0-80% by weight.

6. The method as claimed in claim 1, wherein the test sample is first preheated to the temperature of the NMR probe.

7. The method as claimed in claim 1, wherein the oil sands process stream sample is a sample from a tailings treatment process for optimizing oil sand tailings reclamation.

8. The method as claimed in claim 1, wherein the oil sands process stream sample is a sample from the bitumen extraction process for optimizing the recovery of bitumen.

9. The method as claimed in claim 1, wherein a methylene blue index (MBI) value for a sample is measured using the same approach described for the measurement of fine particle content in the sample by TD-NMR using the FPS raw NMR data sets, except where the PLS calibration reference values are in units of total MB milliequivalents in the sample container.

10. The method as claimed in claim 1, wherein the particle size distribution is for particles having diameters <44 microns, <5.5 microns, and/or <1.9 microns.

11. The method as claimed in claim 10, wherein the content of fine particles at each size can be reported as a percentage of the whole sample or as a percentage of the solids.

12. A method for determining the solids content, fines content and/or particle size distribution in an oil sands process stream test sample comprising bitumen, water, and solids using low-field time-domain NMR, comprising:

(a) initially saturating magnetization of the sample so that essentially no magnetization remains in the +Z axis by applying 10 rapid 90° radio-frequency (RF) pulses to the sample prior to each $T_1$-weighted $T_2$ measurement;

(b) subjecting the sample to either a first combined recovery and transverse relaxation sequence of NMR radio-frequency pulses comprising a $T_1$-weighted $T_2$ measurement with an emphasis on measuring faster relaxing components within the sample, a second combined recovery and transverse relaxation sequence of NMR radio-frequency pulses comprising a $T_1$-weighted $T_2$ measurement with an emphasis on measuring slower relaxing components within the sample, or both;

(c) recording the signal amplitudes from the transverse relaxation ($T_2$) echo trains after incremental longitudinal relaxation ($T_1$) to produce a raw TD-NMR data set that emphasizes faster relaxing components within the sample;

(d) providing a computer which has been programmed to determine the amount of solids, fines and/or particles less than a given particle size in the sample by means of an optimized partial least squares chemometric model relating (i) the faster relaxing raw TD-NMR data sets obtained from a training set of oil sand process samples to the training samples' corresponding reference values obtained from analysis methods for determining bitumen, fine solids less than a given particle size, and/or the particle size distribution of the solids, and (ii) relating the slower relaxing raw TD-NMR data sets obtained from a training set of oil sand process samples to the training samples' corresponding reference values obtained from analysis methods for determining water and non-solids, and using the sample weight to determine the solids content by difference from the non-solids result.

13. The method as claimed in claim 12, wherein the first pulse sequences (FPS) of radio-frequency pulses is such that there are 15 transverse relaxation echoes spaced 0.4 ms apart, acquired at 28 $T_1$ points, exponentially spread from 5 ms through 200 ms, and the final stretch of $T_2$ measurement comprises 50 echoes spaced 2 ms apart, with 24 scans averaged together to improve the signal to noise ratio, resulting in the FPS measurement time of less than 1 minute and the second pulse sequence (SPS) of radio-frequency pulses is such that there are 200 transverse relaxation echoes spaced 0.6 ms apart, acquired at 11 $T_1$ points, exponentially spread from 5 ms through 20000 ms, and the final strech of $T_2$ measurement comprises 200 echoes spaced 20 ms apart, with 4 scans averaged together to improve the signal to noise ratio, resulting in the SPS measurement time of less than 3 minutes.

14. The method of claim 12, wherein one of the reference analysis method is Dean-Stark extraction for measuring bitumen, water, and solids in the training samples.

15. The method of claim 12, wherein one of the reference analysis methods is laser diffraction or wet sieve for measuring the particle size distribution of the solids in the training samples.

16. The method as claimed in claim 12, wherein the test sample is an oil sands process sample or oil sands tailings treatment sample containing solids in the range of 0-80% by weight.

17. The method as claimed in claim 12, wherein the test sample is preheated to the temperature of the NMR probe.

18. The method as claimed in claim 12, wherein a methylene blue index (MBI) value for a sample is measured using the same approach described for the measurement of fine particle content in the sample by TD-NMR using the FPS raw NMR data sets, except where the PLS calibration reference values are in units of total MB milliequivalents in the sample container.

19. The method as claimed in claim 12, wherein the oil sands process stream sample is a sample from a tailings treatment process for use in optimizing oil sand tailings reclamation.

20. The method as claimed in claim 12, wherein the oil sands process stream sample is a sample from the bitumen extraction process for use in optimizing the recovery of bitumen.

21. The method as claimed in claim 12, wherein the measured fine particles can have diameters <44 microns, <5.5 microns, and <1.9 microns as measured by the reference analysis method.

22. The method as claimed in claim 21, wherein the content of fines particles at each size can be reported as a percentage of the whole sample or as a percentage of the solids.

* * * * *